United States Patent
Friebe

(10) Patent No.: US 12,230,387 B2
(45) Date of Patent: *Feb. 18, 2025

(54) PHARMACEUTICAL MANUFACTURING PROCESS CONTROL, SUPPORT AND ANALYSIS

(71) Applicant: Augmenticon AG, Glattbrugg (CH)

(72) Inventor: Matthias Friebe, Glattbrugg (CH)

(73) Assignee: Augmenticon AG, Glattbrugg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/537,255

(22) Filed: Dec. 12, 2023

(65) Prior Publication Data

US 2024/0120079 A1    Apr. 11, 2024

Related U.S. Application Data

(63) Continuation of application No. 17/133,167, filed on Dec. 23, 2020, now Pat. No. 11,894,130.

(30) Foreign Application Priority Data

Dec. 26, 2019    (GB) ...................................... 1919333
Dec. 26, 2019    (GB) ...................................... 1919334
Dec. 26, 2019    (GB) ...................................... 1919335

(51) Int. Cl.
G16H 40/20        (2018.01)
G06F 3/04847      (2022.01)
(Continued)

(52) U.S. Cl.
CPC ......... *G16H 40/20* (2018.01); *G06F 16/9024* (2019.01); *G06Q 10/06316* (2013.01);
(Continued)

(58) Field of Classification Search
None
See application file for complete search history.

(56) References Cited

U.S. PATENT DOCUMENTS 10,366,521 B1    7/2019   Peacock et al.
10,467,534 B1    11/2019  Brent
(Continued)

FOREIGN PATENT DOCUMENTS

WO    2013170204    11/2013
WO    2018106289    6/2018
(Continued)

OTHER PUBLICATIONS

Henderson and Feiner, IEEE International Symposium on Mixed and Augmented Reality 2009, pp. 135-144 (ISBN 978-1-4244-5389-4/09).
(Continued)

*Primary Examiner* — Frank S Chen
(74) *Attorney, Agent, or Firm* — Nemphos Braue LLC; Michael Antone

(57) ABSTRACT

A computer apparatus and computer-implemented process for generating a batch record (BR) from a master batch record (MBR) during manufacture of a batch of pharmaceutical product. In the control software, a graphical analysis interface is provided for processing graphs of spectroscopic or chromatographic analysis. A group of fields in the MBR is assigned to the analysis. The operator wears an augmented reality headset and uses this to capture an image of a graph from an instrument display. The graph image is then processed to extract the graph and its metadata, and then further processed to find peaks and assign attribute labels to the peaks, and thus populate the analysis fields. Overlay images are then transmitted to AR headset to present to the operator the populated analysis fields. The operator then accepts or
(Continued)

rejects the populated analysis fields by issuing user interface commands.

17 Claims, 20 Drawing Sheets

(51) Int. Cl.
| | | |
|---|---|---|
| G06F 16/901 | (2019.01) | |
| G06Q 10/0631 | (2023.01) | |
| G06Q 10/0639 | (2023.01) | |
| G06Q 10/10 | (2023.01) | |
| G06Q 50/04 | (2012.01) | |
| G06V 20/20 | (2022.01) | |
| G16H 70/40 | (2018.01) | |
| H04N 7/14 | (2006.01) | |

(52) U.S. Cl.
CPC ..... *G06Q 10/06395* (2013.01); *G06Q 10/103* (2013.01); *G06Q 50/04* (2013.01); *G06V 20/20* (2022.01); *G16H 70/40* (2018.01); *H04N 7/147* (2013.01); *G06F 3/04847* (2013.01)

(56) References Cited

U.S. PATENT DOCUMENTS

| | | |
|---|---|---|
| 2004/0193022 A1 | 9/2004 | Torii |
| 2004/0219054 A1 | 11/2004 | Sugawara |
| 2012/0007852 A1 | 1/2012 | Morate et al. |
| 2012/0101837 A1 | 4/2012 | McCorkle |
| 2013/0010068 A1 | 1/2013 | Tiernan et al. |
| 2013/0038633 A1 | 2/2013 | Maggiore |
| 2013/0049976 A1 | 2/2013 | Maggiore |
| 2013/0278635 A1 | 10/2013 | Maggiore |
| 2016/0055674 A1 | 2/2016 | Mullins et al. |
| 2016/0132046 A1 | 5/2016 | Beoughter et al. |
| 2016/0328887 A1 | 11/2016 | Elvezio et al. |
| 2016/0364913 A1 | 12/2016 | Montaigne |
| 2017/0142324 A1 | 5/2017 | Jost et al. |
| 2018/0109083 A1 | 4/2018 | Fenker |
| 2018/0165978 A1 | 6/2018 | Wood et al. |
| 2018/0211447 A1 | 7/2018 | Spayd |
| 2018/0356878 A1 | 12/2018 | Dudekula et al. |
| 2018/0357823 A1 | 12/2018 | Duff et al. |
| 2018/0357922 A1 | 12/2018 | Dutta et al. |
| 2019/0316912 A1 | 10/2019 | Maggiore et al. |
| 2019/0362556 A1 | 11/2019 | Ben-Dor et al. |
| 2020/0125064 A1 | 4/2020 | Frick et al. |
| 2020/0188028 A1 | 6/2020 | Feiner et al. |

FOREIGN PATENT DOCUMENTS

| | | |
|---|---|---|
| WO | 2018152629 | 8/2018 |
| WO | 2018197349 | 11/2018 |

OTHER PUBLICATIONS

Henderson and Feiner, IEEE International Symposium on Mixed and Augmented Reality 2011, pp. 191-200 (ISBN 978-1-4577-2185-4/10).

Philip Wenig, Label Chromatogram Peaks & Scans, https://spectrometrylab.wordpress.com/2016/08/01/label-chromatogram-peaks-scans/, Aug. 1, 2016.

Tom O'Haver, Integration and peak area measurement, https://terpconnect.umd.edu/~toh/spectrum/Integration.html.

Kim et al, Revisiting Trends in Augmented Reality Research: A Review of the 2nd Decade of ISMAR (2008-2017), Sep. 1, 2018, IEEE Transactions on Visualization and Computer Graphics pp. (99):1-1 (DOI: 10.1109/TVCG.2018.2868591).

| Record the chemistry cell number used for the production and record the pressure within the cell (- 400 Pa ± 50Pa). | Cell<br>No. | Pressure<br>Pa |
|---|---|---|
| Perform a line clearance of waste material from the chemistry cell | | |
| Re-inspect the scavenger vial (V-8) to ensure the solution is fully mixed and homogenized.<br>1. Open a new 5mL syringe and attach a new needle<br>2. remove 4mL from Bottle B-x and add this to HPLC Buffer bottle B-y<br>3. Connect a mini spike filter to the B-y bottle | | |
| Connect a mini spike filter to the B-z bottle. | | |
| Unpack the synthesis cassette and continue as follows:<br>• Perform a general inspection of the unit to ensure all tubes are fully located on the cassette with no tube damaged or pinched<br>• Check the presence of all rotating valves on rear of unit<br>  o Rotate each valve to verify none is stuck or broken.<br>  o Place all valve slots into the vertical position.<br>• Check that the reactor needle is at the bottom of the reactor vial.<br>• Establish the product out-line luer connections.<br>• Open and position a conditioned Sep-PAK Light QMA cartridge on the available front luer connection (by reconnecting tube to top of cartridge).<br>• Confirm the rear luer tapered connecting tube is securely inserted.<br>If in doubt discard cassette and start over | | |

FIG. 9

| Actions | Initial |
|---|---|
| Empty the Nitrogen collection bag:<br><br>• Carefully inspect the $N_2$ collection bag and waste tubes for leaks.<br><br>• Caution: Do not stretch/dislocate the connecting tube from the unit.<br><br>Replace bag if in doubt. | |
| Inspect the $^{18}O$ water recovery vial:<br><br>• If it is more than half full, replace with a new sealed 15mL vial labelled accordingly.<br><br>• Empty the volume from the vial into the O-18 bottle in the waste room for recycling | |
| Inspect the waste container:<br><br>• Check the levels of liquid waste.<br><br>• If above maximum level, empty into container labelled "long half-life organic waste". | |
| Inspect the V-vial - DO NOT INTERFERE WITH SEPTUM.<br><br>• Check the Teflon $^{18}F$ delivery line for damage.<br><br>• Verify that peek tubing for the $^{18}F$ delivery line is placed to touch the bottom of the V-shape in the reception vial. | |
| Open the local isolation valve at the rear of the module and verify that the system pressure is approximately 3 bar. If there is no or insufficient pressure, verify that the Nitrogen gas inlets are open on the external manifold before carrying out any trouble shooting.<br><br>Specification 2 - 5 bars | _____bar |

FIG. 10

| Record the chemistry cell number used for the production and record the pressure within the cell (- 400 Pa ± 50Pa). | Cell | Pressure |
|---|---|---|
| | No. | Pa |
| Perform a line clearance of waste material from the chemistry cell | | |
| Re-inspect the scavenger vial (V-8) to ensure the solution is fully mixed and homogenized.<br>1. Open a new 5mL syringe and attach a new needle<br>2. remove 4mL from Bottle B-x and add this to HPLC Buffer bottle B-y<br>3. Connect a mini spike filter to the B-y bottle | | |
| Connect a mini spike filter to the B-z bottle | | |
| Unpack the synthesis cassette and continue as follows:<br><br>• Perform a general inspection of the unit to ensure all tubes are fully located on the cassette with no tube damaged or pinched<br><br>• Check the presence of all rotating valves on rear of unit<br>  ○ Rotate each valve to verify none is stuck or broken.<br>  ○ Place all valve slots into the vertical position.<br><br>• Check that the reactor needle is at the bottom of the reactor vial.<br><br>• Establish the product out-line luer connections.<br><br>• Open and position a conditioned Sep-PAK Light QMA cartridge on the available front luer connection (by reconnecting tube to top of cartridge).<br><br>• Confirm the rear luer tapered connecting tube is securely inserted.<br><br>If in doubt discard cassette and start over | | |

FIG. 11

| Actions | Initial |
|---|---|
| Empty the Nitrogen collection bag:<br>• Carefully inspect the $N_2$ collection bag and waste tubes for leaks.<br>• Caution: Do not stretch/dislocate the connecting tube from the unit.<br>Replace bag if in doubt. | |
| Inspect the $^{18}O$ water recovery vial:<br>• If it is more than half full, replace with a new sealed 15mL vial labelled accordingly.<br>• Empty the volume from the vial into the O-18 bottle in the waste room for recycling | |
| Inspect the waste container:<br>• Check the levels of liquid waste.<br>• If above maximum level, empty into container labelled "long half-life organic waste" | |
| Inspect the V-vial - DO NOT INTERFERE WITH SEPTUM.<br>• Check the Teflon $^{18}F$ delivery line for damage.<br>• Verify that peek tubing for the $^{18}F$ delivery line is placed to touch the bottom of the V-shape in the reception vial. | |
| Open the local isolation valve at the rear of the module and verify that the system pressure is approximately 3 bar. If there is no or insufficient pressure, verify that the Nitrogen gas inlets are open on the external manifold before carrying out any trouble shooting.<br>Specification 2 - 5 bars | _____bar |

FIG. 12

| Components and reagents | Document | Lot number | Expiry |
|---|---|---|---|
| Reagent kit for [18F]PSMA1007 synthesis | N5R-3088E | | |
| [18F]PSMA1007 precursor | P5R-3100E | | |
| Tetrabutylammonium hydrogen carbonate | N5R-3054E | | |
| Synthesis set [18F]PSMA1007 | P2R-3030E | | |
| Neptis PSMA1007 disposable cassette | N2R-3017E | | |
| Neptis formulation disposable cassette | N2R-3018E | | |
| Dispensing set | P2R-4001E | | |
| HPLC mobile phase rinsing 7/3 MeCN/H₂O | P5R-4063E | | |
| HPLC column Atlantis T3 OBD 5µm | V3R-3016E | | |
| Mobile phase semi-prep HPLC [18F]PSMA1007 | P5R-3102E | | |

FIG. 14A

| Components and reagents | Document | Lot number | Expiry |
|---|---|---|---|
| Reagent kit for [18F]PSMA1007 synthesis | N5R-3088E | Lot No. 1234 | 07/2020 |
| [18F]PSMA1007 precursor | P5R-3100E | Lot No. 2345 | 05/2021 |
| Tetrabutylammonium hydrogen carbonate | N5R-3054E | Lot No. 9876 | 12/2020 |
| Synthesis set [18F]PSMA1007 | P2R-3030E | Lot No. 4321 | 11/2020 |
| Neptis PSMA1007 disposable cassette | N2R-3017E | | |
| Neptis formulation disposable cassette | N2R-3018E | Lot No. 5555 | 09/2022 |
| Dispensing set | P2R-4001E | Lot No. 9164 | 06/2023 |
| HPLC mobile phase rinsing 7/3 MeCN/H₂O | P5R-4063E | Lot No. 865 | 07/2022 |
| HPLC column Atlantis T3 OBD 5µm | V3R-3016E | Lot No. 3471 | 07/2020 |
| Mobile phase semi-prep HPLC [18F]PSMA1007 | P5R-3102E | Lot No. 8235 | 12/2025 |

FIG. 14B

Equipment
Isolator                    ISO-........
Neptis synthesizer          APP-........
Precision balance           APP-........
Dose calibrator             APP-........

FIG. 15A

Equipment
Isolator                    ISO-15
Neptis synthesizer          APP-205
Precision balance           APP-260
Dose calibrator             APP-107

FIG. 15B

PHARMACEUTICAL MANUFACTURING PROCESS CONTROL, SUPPORT AND ANALYSIS

CROSS-REFERENCE TO RELATED APPLICATIONS

This application is a continuation application of U.S. patent application Ser. No. 17/133,167 filed 2020 Dec. 23, which claims the benefit of and priority to United Kingdom Application Nos. GB1919333.3, GB1919334.1, and GB1919335.8 filed 26 Dec. 2019 and is related to U.S. patent application Ser. Nos. 18/537,217 and 18/537,321 filed on even date herewith as docket numbers HIP-004-011-USA and HIP-004-011-USC that are also continuation applications of U.S. patent application Ser. No. 17/133,167, the disclosure of each is incorporated herein by reference in its entirety.

STATEMENT REGARDING FEDERALLY SPONSORED RESEARCH OR DEVELOPMENT

Not Applicable

BACKGROUND OF THE INVENTION

Field of the Invention

The invention relates to quality control procedures in a pharmaceutical manufacturing process, to providing support for a pharmaceutical manufacturing process, and to image analysis procedures for manufacturing and quality control in a pharmaceutical manufacturing process.

Background Art

In large-scale pharmaceutical manufacturing it is common to use reactor assemblies and dispenser (or dosing) assemblies. In small-scale pharmaceutical manufacturing it is common to use synthesis modules for chemical synthesis involving multiple liquid reagents each provided in a vial. A synthesis module may comprise a substrate with a docking station for each vial involved in the synthesis, as well as one or more docks for vials that are to receive the synthesis products and waste products.

Decentralised manufacture of pharmaceuticals has become standard practice due to the opportunities to save costs through globalisation and also due to trade restrictions imposed by some notable markets, including China, India and Brazil, which require in-country manufacturing.

Local manufacture of pharmaceuticals is also necessary for certain compounds, such as radiopharmaceuticals that contain isotopes with short half-lives. For example, 18F & 68Ga isotopes used as positron emitters in positron emission tomography (PET) scans have half-lives of 109 & 68 minutes respectively, and the various iodine isotopes (123I, 124I, 125I, 131I) used as tracers in medical imaging and systemic radiotherapy have half-lives in the range of 6.5 hours to 60 days. Other mainly metal-based radioisotopes such as Pb-212, Lu-177, Y-90, Re-186/Re-188, Ac-225 and Ra-223 intended for use in systemic radiotherapy have half-lives ranging from 10.6 hours to 11.4 days. Distribution of a radiopharmaceutical to the clinic must be rapid, since the compounds lose dose and therewith efficacy after a few half-lives have elapsed.

Local or decentralised manufacture causes challenges to maintaining quality and uniformity of practice. In particular, the quality of remote training and supervision of the local manufacturing staff becomes key. Monitoring and supervision also become less easy compared with a single large manufacturing site.

Manufacturing of pharmaceuticals is performed according to and controlled by formal regulations, instructing the operator on how to perform the tasks which collectively implement the chemical and physical steps leading to a finished pharmaceutical product. Such regulations are usually complied with through a master batch record (MBR), a document generated by the holder of the marketing authorisation or the sponsor of a study to ensure compliance with established procedures, granted marketing approvals and sometimes also intellectual property licenses. Completion of an MBR during manufacturing of a batch is akin to filling out a complicated form full of check boxes and other entries. A completed MBR is referred to as a batch record (BR), i.e. a BR is a completed MBR for a specific batch, whereas the MBR is merely the template. The BR has the role of documenting the full process from preparatory work via the setup of the campaign, the execution of the process, equipment cleaning procedures between batches or during a batch and dispensing procedures.

In a cleanroom environment with full gowning requirements, it is necessary, or at least highly desirable, to provide "hands-free" access to the MBR/BR so that the operators can fill it out conveniently and without causing contamination.

Proper documentation is key to all pharmaceutical manufacturing activity including for: preparation, quality control and release. It is of utmost importance to avoid errors, not to miss critical data and to reduce the risk of falsification and general fraud. The comprehensive requirements placed on the BR and other release documents to include all relevant data can lead to very lengthy documents ranging typically from as little as 100 pages to 4,000 pages or more. The compilation of documentation is thus an integral component of the pharmaceutical manufacturing process, just the same as the physical and chemical process components and the testing and analysis components and is, moreover, one that is intimately interwoven into these other components, not a parallel track that can be done independently.

In a traditional pharmaceutical documentation process using paper, i.e. hard copy, every page of the document is compiled by hand. The document will include printouts of machine reports, chromatograms which are literally stuck into the document, and diverse hand-written entries for values of measuring parameters displayed on various instruments and gauges that have been read-off by the operator. The time needed to compile the documentation often exceeds all other contributions to the time needed for the manufacturing process.

Especially in the field of radiopharmaceuticals, there is an overriding time criticality to the manufacturing process imposed by the short half-lives of the radioisotopes being used. For example, if a first batch takes a time of one half-life to make (e.g. 109 minutes for 18F), and a second batch takes twice as long to complete (e.g. 218 minutes), then ceteris paribus there would be twice as many product-doses in the first batch compared to the second batch. In other words, in the field of radiopharmaceutical preparation, a reduction in the time needed to prepare a release document will lead directly to increased revenue.

A paperless, or at least less-paper, solution is to integrate the various machines and instruments that provide output for the documentation into a computer network and more especially into the electronic record management system software used to compile the electronic BR from an electronic MBR. The same is the case for other paperless records of relevance for pharmaceutical manufacturing, e.g. line clearance between manufacturing different batches. However, this is not so straightforward to do in practice. The various machines and instruments used in a particular cleanroom for pharmaceutical manufacture will typically come from a large number of different specialist manufacturers and some may be quite old, e.g. 10 or 20 years old. They represent in many cases expensive capital equipment and so it is not economic simply to replace them in order to enable convenient state-of-the-art network integration. Consequently, it is often impractical or at least highly costly to provide suitable hardware interfaces for every machine and instrument that supplies input to the documentation. In addition, even if all the equipment is connected effectively to a common network, a software integration is also required, so that the electronic record management system responsible for compiling the BR or other document knows what data to take from each machine and when during the overall process. Writing and configuring suitable software to do this is of course also a major project of itself.

Various disclosures are known which relate to the use of augmented reality (AR) headsets to assist in preparation of documentation and to support operators in performing laboratory procedures, namely:

US2013010068A1
US2013278635A1
US2016132046A1
US2016055674A1
US2018211447A1
WO2013170204A1
WO2018106289A1.

Some parameter values that are required by the BR can be extracted from the spectrograph without any subjectivity, such as molecular peak positions. Other parameter values involve some subjective interpretation by an expert. For example, the BR may require entry of the abundance levels of the molecules associated with the peaks in the chromatogram, these mostly being impurity species that can only be present below a certain abundance for the pharmaceutical product to meet specification. To determine the abundance level, a baseline must first be inserted into the graph. Other parameters whose determination may involve subjective expert interpretation are:

peak separation near the resolution limit (e.g. is the feature one peak or two peaks? If two peaks, how is the overall peak area to be apportioned between the two peaks?)
peak start and end wavelengths
allocation of peaks to molecules (e.g. there may be two or more molecules associated with the same peak wavelength)

FIG. 16 is an example chromatogram where the peaks correspond to different haemoglobin variants: HbA0 non-glycated haemoglobin; HbA2 normal variant haemoglobin; HbA1c glucose-bound haemoglobin etc. Two baselines are shown; a first with a dashed line and, slightly below that, another with a dot-dashed line. The y-axis is in arbitrary units (AU) reflecting the absorption of the compounds at a certain wavelength (e.g. in the UV range) or counts per unit time (e.g. gamma-, beta- or alpha-rays). The x-axis is in units of time (e.g. minutes as shown) based on the retention time of analytes on the solid-phase extraction material, in which the most hydrophilic compounds elute first followed by the less hydrophilic compounds in order of decreasing hydrophilicity when a so called reverse-phase material is used as the solid phase or vice versa with a "normal"-phase silica-based solid phase material. The relative abundance of each compound can be determined from the relative magnitudes of the integrals of each peak both for visible, UV or IR spectroscopic (light) signals and radiation signals in case of radiation detection. Thus, either method allows for a quantitative assessment of the chemical purity through light-signals or of the radiochemical purity through radioactive particle detection.

It is evident that the integrated intensity of the various labelled peaks, corresponding to the abundance level of each species, will be significantly different depending on which of these two baselines is used. The interpretation difference that has caused the different placement of these two baselines is based on the expert making a different decision regarding the significance of the unlabelled peak group at around 1 minute. One expert has dismissed this peak group as an artefact, presumably since the expert has specific knowledge that this is the case, whereas the other expert has included this peak group as signal of significance. The baseline may be entered by the expert on the display of the computer associated with the spectrographic instrument using a graphical user interface, and then the computer calculates the integrated intensity of each peak, and from that displays an abundance level together with the peak wavelength.

Since the chromatogram interpretation can have a significant impact on the analytical result, it is important that it is done properly. However, owing to the underlying complexity of the results, such as the interplay between signal and noise, the possibly presence of artefacts which look like signal but are not, and the possibility that peaks will overlap and be close to or under the resolution limit, it is often the case that some aspects of the interpretation of a given graph will be subjective. In an ideal situation, it should be the person who is ultimately responsible for the quality of the drug product (in the EU the Qualified Person, QP) that should make the final decision as to whether the analysis and interpretation of the chromatogram was done properly and that the analytical result can be adopted as being reliable.

In a paper-based system, the expert will transcribe the peak values, abundance values and other parameters to be noted into the corresponding fields or fields of the BR as well as printing out the graph with baseline annotation and possibly with other annotations added by the expert (e.g. labelling of peaks with molecules). The annotated print-out of the graph is then included in the BR.

In a more modern context, it is likely that a state-of-the-art chromatographic or spectroscopic instrument will allow export of electronic copies of the results, including not only the chromatogram or spectrogram, but also the parameter values extracted from the spectrogram and other intermediate results (such as peak values, baseline, peak integrated intensity). The exported file can then be imported into an electronic record management system hosting the MBR which runs a software process to extract the data from the imported file and to transcribe the extracted data to populate the relevant MBR field(s) and thus create the relevant portion of the BR.

However, while this integration between chromatographic/spectroscopic instruments and the (M)BR's electronic record management system is doable, it requires a major project to implement. In particular, it needs to be borne in mind that there is likely to be a host of different spectroscopic instruments from diverse manufacturers in any particular site, some of which may be quite old and lack modern IT interfaces. Chromatographic or spectroscopic instruments often represent major pieces of capital equipment and so it is not economic simply to replace them in order to enable convenient state-of-the-art network integration. In addition, even if the instruments are all state-of-the-art and connected effectively to a common computer network, a software integration is also required, so that the electronic record management system responsible for compiling the BR knows what data to take from each instrument and when during the overall pharmaceutical manufacturing process. Writing and configuring suitable software to do this is of course also a major project of itself.

What is also needed is a way to speed up the electronic record completion part of the pharmaceutical manufacturing process without requiring a network integration of the multifarious pieces of cleanroom equipment combined with a software integration with the electronic MBR/BR management system.

Moreover, the assembly of synthesis modules can be complex. It is necessary to dock each vial in the correct location and make the connection reliably. It is additionally often necessary to make some fluid fitting connections (typically of the luer type) between vials by manipulating flexible tubing and forming seals at each end. Various errors are possible. The wrong vial may be docked at a particular station. A vial may be selected which contains the correct reagent, but perhaps in the wrong quantity, or perhaps a vial has been taken containing reagent which is out-of-date.

In the field of radiopharmaceuticals, there is also an overriding time criticality to the manufacturing process imposed by the short half-lives of the radioisotopes being used. For example, the half-life of the radioisotope 18F is only 109 minutes. However, the imperative on the operator to perform the assembly tasks quickly clearly creates a tension with the need to avoid mistakes.

SUMMARY OF THE INVENTION

According to one aspect of the disclosure there is provided a computer apparatus configured to generate a batch record, BR, during manufacture of a batch of pharmaceutical product by populating a master batch record, MBR, the computer apparatus comprising:
 a process data structure defining a sequence of manufacturing process steps required to be carried out to manufacture a batch, the batch manufacturing process steps involving respective operator actions, wherein the operator actions include performing at least one of a chromatographic and spectroscopic analysis of the batch using a chromatographic or a spectroscopic instrument;
 an MBR comprising a plurality of content items and associated fields, wherein the fields are to be populated as an operator progresses through the operator actions, the MBR including a group of fields relating to the analysis;
 a mapping data structure that provides links between ones of the operator actions to ones of the content items and associated fields, including for the analysis; and
 a control module configured to:
 establish a data communication connection to an augmented reality, AR, headset worn by an operator responsible for manufacturing the batch;
 receive scene image data from the connected AR headset of a graph image captured by the AR headset showing results of the analysis;
 process the received scene image data to extract a graph and associated graph metadata from the graph image, wherein the graph includes a plurality of peaks;
 interpret the peaks of the graph with reference to the graph metadata to obtain peak data;
 populate the analysis fields with reference to the mapping data structure with the graph, metadata associated with the graph and peak data associated with the graph;
 transmit overlay image data to the connected AR headset to present to the operator the populated analysis fields; and
 receive user interface commands from the connected AR headset to accept or reject the populated analysis fields.

Chromatographic results may be from thin layer chromatography (TLC) or column-based high-pressure liquid chromatography (HPLC), for example. Spectroscopic results may be from nuclear magnetic resonance (NMR) spectroscopy or mass spectroscopy (MS), for example. The features to be extracted may be different for different measurements. In MS, for example, the relative signal position associated with a certain mass-peak is crucial for interpretation. In proton NMR, for example, the relative position, shape and the integrated area of the peaks are relevant.

In certain embodiments, the control module is further configured to:
 transmit overlay image data to the connected AR headset to present to the operator the graph and positioned thereon a baseline which is to be taken as an ordinate zero line;
 receive user interface commands from the connected AR headset to reposition the baseline during which the baseline is shown interactively to the operator by amending the overlay image data and to accept the baseline; and
 populate an analysis field with the accepted baseline.

The peak data may include position values for the peaks and/or integral values for the peaks.

The control module may be further configured to assign attribute labels to at least some of the peaks. The attribute labels may be assigned having regard to known groupings of peaks that are characteristic of the presence of a single atomic or molecular species (so-called fingerprint) as can be the case, for example, in NMR spectroscopy or mass spectroscopy.

Attribute labels may be assigned to peaks by the computer apparatus in different ways. They may be assigned by processing the graph. They may be assigned by receiving user interface commands from the connected AR headset that specify the attribute label assignment, e.g. the operator could be making decisions on the labels based on his/her expertise or based on other results that are available to him/her. They may be assigned by processing the graph image in the case that the attribute label assignment was already displayed in the graph image captured by the AR headset, and this information can be extracted from the graph image. The control module may be further configured to determine relative abundance values between the attributes based on a comparison of the peak integral values. The control module may be further configured to interpret the graph with reference to pre-existing and already interpreted graphs stored in a graph library, wherein the pre-existing graphs are selected based on being from the same kind of analysis using the same kind of instrument on a different batch of the same pharmaceutical product.

In some embodiments, the control module is further configured to perform a quality control, QC, check of the batch based on an automated analysis of what has been entered in the analysis fields of the BR, wherein the quality control check compares the analysis field entries with what is permitted in those field entries according to a specification that forms part of the MBR. The QC check then outputs a QC check outcome. Example outcomes of such a QC check may be that the results indicate that the batch meets or does not meet specification. A finer set of outcomes may also include other outcomes such as the results indicate that the batch may not meet specification. In other words, the automated analysis leaves some doubt as to whether the batch is OK or not. This can be a useful prompt to a qualified person to look at the BR more closely. Another potentially useful outcome would be that that the results indicate a systematic error in the completion of the BR. For example, some fields could be blank, or some numerical field entries could contain values that clearly cannot be true in that they lie outside any plausible range. This could be a prompt for the operator to re-check the entry.

As part of supporting QC and batch release, the control module may be further configured to transmit the BR and QC check outcome to a workstation for review by a qualified person, QP. The role of the QP in the process is to make a batch release decision based on the available information as documented in the BR. The control module is configured to receive the QP's batch release decision from the workstation and enter it in a corresponding field of the BR. To further support the QP, the control module may be configured to record at least a subset of scene image data received from the connected AR headset during the manufacture of the batch of pharmaceutical product, said recorded scene image data including video footage; and transmit at least some of the recorded scene image data to the workstation for review by the QP. The QP would thus not only have available the BR, but also contemporaneous video footage. A further useful measure to support the QP is for the control module to be configured to establish both a live audio communication channel between the QP's workstation and the operator's AR headset to permit the QP to speak with the operator and a live video communication channel for transmitting live video feed from the AR headset to the QP workstation. These two channels enable the QP to view a live video feed from the AR headset while being able to speak with the operator, e.g. while directing the operator to look at certain relevant things in the cleanroom through the AR headset, where the QP is viewing the live footage from the operator's AR headset.

According to another aspect of the disclosure, there is provided a computer-implemented process for generating a batch record, BR, by populating a master batch record, MBR, as part of manufacture of a batch of pharmaceutical product by an operator wearing an augmented reality, AR, headset, the process comprising:

providing a process data structure defining a sequence of manufacturing process steps required to be carried out to manufacture a batch, the batch manufacturing process steps involving respective operator actions, wherein the operator actions include performing at least one of a chromatographic and spectroscopic analysis of the batch using a chromatographic or a spectroscopic instrument;

establishing a data communication connection between the AR headset and a computer apparatus configured to control the generation of the BR during manufacture;

providing the computer apparatus with an MBR comprising a plurality of content items and associated fields, wherein the fields are to be populated as an operator progresses through the operator actions, the MBR including a group of fields relating to the analysis;

providing the computer apparatus with a mapping data structure that provides links between ones of the operator actions to ones of the MBR content items and associated fields, including for the analysis;

processing the received scene image data to extract a graph and associated graph metadata from the graph image, wherein the graph includes a plurality of peaks;

interpreting the peaks of the graph with reference to the graph metadata to obtain peak data;

populating the analysis fields with reference to the mapping data structure with the graph, the graph metadata and graph peak data;

transmitting overlay image data to the connected AR headset to present to the operator the populated analysis fields; and receiving user interface commands from the connected AR headset to accept or reject the populated analysis fields.

Another aspect of the disclosure provides a computer program product bearing machine-readable instructions for performing the computer-implemented process.

In summary, a computer apparatus and computer-implemented process for generating a batch record (BR) from a master batch record (MBR) during manufacture of a batch of pharmaceutical product. In the control software, a graphical analysis interface is provided for processing graphs of spectroscopic or chromatographic analysis. A group of fields in the MBR is assigned to the analysis. The operator wears an augmented reality headset and uses this to capture an image of a graph from an instrument display. The graph image is then processed to extract the graph and its metadata, and then further processed to find peaks and assign attribute labels to the peaks, and thus populate the analysis fields. Overlay images are then transmitted to AR headset to present to the operator the populated analysis fields. The operator then accepts or rejects the populated analysis fields by issuing user interface commands.

According to one aspect of the disclosure there is provided a computer apparatus configured to generate a batch record, BR, during manufacture of a batch of pharmaceutical product by populating a master batch record, MBR. The computer apparatus comprises:

a process data structure defining a sequence of manufacturing process steps that are required to be carried out to manufacture a batch, the manufacturing process steps involving respective operator actions;

an MBR comprising a plurality of content items and associated fields, wherein the fields are to be populated as an operator progresses through the operator actions;

a mapping data structure that links operator actions to content items and associated fields; and a control module configured to:

establish a data communication connection to an augmented reality, AR, headset worn by an operator responsible for manufacturing the batch;

transmit overlay image data to the connected AR headset, the overlay image data presenting ones of the content items and associated fields to the operator in a way that follows the operator's progression through the operator actions as determined with reference to the mapping data structure and that is responsive to the operator populating the MBR fields;

receive user interface commands from the connected AR headset; and populate fields of the MBR, as presented to the operator in the overlay image data, responsive to receipt of the user interface commands.

In certain embodiments, the control module is further configured to modify the overlay image data so that the content items and/or associated fields are rendered having regard to a criticality grading of the operator actions. The control module may be further configured to store a plurality of operator profiles relating to at least one of: operator skill and operator track-record of individual persons, and wherein the criticality grading takes account of an operator profile selected for the operator carrying out the operator actions. The content items may include text content and the overlay image data is modified by adding visually perceptible markings to distinguish between different portions of the text content having regard to said criticality grading.

The computer apparatus may further comprise a library of training units, e.g. as saved in a database. The training units may comprise one or more of video clips, stills images, text and audio. Each training unit is associated with a specific operator action, group of operator actions or manufacturing process step. The mapping data structure links operator actions and training units, so for example if an operator needs or requests help in performing a particular action during the manufacturing process, a suitable training unit can be delivered to the operator through the AR headset.

One example of AR support is when the process data structure includes a definition of a group of the operator actions that relate to assembly of a synthesis module by attaching a plurality of vials to specific ones of respective docking stations on the synthesis module.

In this example, the control module may be further configured to: receive scene image data from the connected AR headset of at least one image captured by the AR headset; process the received scene image data to perform vial identification on any vials found in the scene image data by reading a machine-readable code attached to any such vial; and in response thereto transmit data to the connected AR headset providing feedback information extracted through each code.

In this example, the control module may be further configured to: receive scene image data from the connected AR headset of at least one image captured by the AR headset; process the received scene image data to identify any vials found in the scene and to identify any docking stations in the scene, at least ones that relate to identified vials, and in response thereto; transmit data to the connected AR headset conveying at least one of: an indication of docking station in case of an undocked vial; and an indication of correctness of docking station in case of a docked vial.

On completion of the group of the operator actions relating to assembly of the synthesis module, the control module may be further configured to: receive scene image data from the connected AR headset of at least one image captured by the AR headset; process the received scene image data to perform a holistic verification of correct synthesis module assembly; and responsive thereto transmit data to the connected AR headset conveying an indication of correctness of the assembly.

In another example, the control module is further configured to:
  receive scene image data from the connected AR headset of at least one image captured by the AR headset, wherein the at least one image is of a display of a piece of equipment used during the manufacture of the batch of pharmaceutical product;
  process the received scene image data to extract at least one of: graphical data, including a graph and associated graph metadata; and text data;
  map the extracted graphical and/or text data to at least one field of the MBR with reference to the mapping data structure;
  populate the at least one field according to the mapping; and
  transmit overlay image data to the connected AR headset to present to the operator the at least one field as populated according to the extracted graphical and/or text data.

In this example, the control module may be further configured to: receive a user interface command to select at least one field of the MBR from the connected AR headset; associate the at least one selected field with the received scene image data from the equipment display; and apply the data extraction and mapping to the at least one selected field.

In some embodiments, the control module is further configured to perform a quality control, QC, check of the batch. The QC check may be based on an automated analysis of what has been entered in the fields of the BR. The quality control check compares the field entries with what is permitted in those field entries according to a specification that forms part of the MBR. Example outcomes of such a QC check may be that the results indicate that the batch meets or does not meet specification. A finer set of outcomes may also include other outcomes such as the results indicate that the batch may not meet specification. In other words, the automated analysis leaves some doubt as to whether the batch is OK or not. This can be a useful prompt to a qualified person to look at the BR more closely. Another potentially useful outcome would be that that the results indicate a systematic error in the completion of the BR. For example, some fields could be blank, or some numerical field entries could contain values that clearly cannot be true in that they lie outside any plausible range. This could be a prompt for the operator to re-check the entry. As part of supporting QC and batch release, the control module may be further configured to transmit the BR and QC check outcome to a workstation for review by a qualified person, QP. The role of the QP in the process is to make a batch release decision based on the available information as documented in the BR. The control module is configured to receive the QP's batch release decision from the workstation and enter it in a corresponding field of the BR. To further support the QP, the control module may be configured to record at least a subset of scene image data received from the connected AR headset during the manufacture of the batch of pharmaceutical product, said recorded scene image data including video footage; and transmit at least some of the recorded scene image data to the workstation for review by the QP. The QP would thus not only have available the BR, but also contemporaneous video footage. A further useful measure to support the QP is for the control module to be configured to establish both a live audio communication channel between the QP's workstation and the operator's AR headset to permit the QP to speak with the operator and a live video communication channel for transmitting live video feed from the AR headset to the QP workstation. These two channels enable the QP to view a live video feed from the AR headset while being able to speak with the operator, e.g. while directing the operator to look at certain relevant things in the cleanroom through the AR headset, where the QP is viewing the live footage from the operator's AR headset.

According to another aspect of the disclosure, there is provided a computer-implemented process for generating a batch record, BR, by populating a master batch record, MBR, as part of manufacture of a batch of pharmaceutical product by an operator wearing an augmented reality, AR, headset, the process comprising:
  providing a process data structure defining a sequence of manufacturing process steps required to be carried out to manufacture a batch, the batch manufacturing process steps involving respective operator actions;
  establishing a data communication connection between the AR headset and a computer apparatus configured to control the generation of the BR during manufacture;
  providing the computer apparatus with an MBR comprising a plurality of content items and associated fields, wherein the fields are to be populated as an operator progresses through the operator actions;
  providing the computer apparatus with a mapping data structure that links operator actions to content items and associated fields;
  transmitting overlay image data from the computer apparatus to the connected AR headset, the overlay image data presenting ones of the content items and associated fields to the operator in a way that follows the operator's progression through the operator actions as determined with reference to the mapping data structure and that is responsive to the operator populating the MBR fields; and
  generating the BR by populating the fields of the MBR, as presented to the operator in the overlay image data, responsive to receipt of respective user interface commands from the connected AR headset.

A further aspect of the disclosure provides a computer program product bearing machine-readable instructions for performing the computer-implemented process.

In summary, a computer apparatus and computer-implemented process are provided for generating a batch record from a master batch record during manufacture of a batch of pharmaceutical product. In the control software, a process data structure defines the manufacturing steps and breaks them down into actions to be performed by an operator and mapping data structure links these operator actions to content items and associated fields in the master batch record. The operator wears an augmented reality headset 10 and receives overlay images of the content items and fields as the operator progresses through the operator actions. Through a user interface, the operator can then populate the fields as they are completed with reference to the mapping data structure. The overlay images can highlight content items according to their criticality to reduce risk of operator errors and also highlight field entries that are absent or which do not meet specification.

According to one aspect of the disclosure there is provided a computer apparatus configured to provide a process control function during manufacture of a batch of pharmaceutical product to check whether a piece of equipment has been set up correctly to carry out a manufacturing process step, the computer apparatus being configured to:
  establish a data communication connection to an augmented reality, AR, headset;
  receive scene image data from the connected AR headset of an image captured by the AR headset;
  process the received scene image data to identify an image of the piece of equipment and make a determination of its correct or incorrect set up; and
  transmit data to the connected AR headset conveying an indication of the correct or incorrect set up.

In some embodiments, the processing attempts to segment a pre-defined plurality of objects from the equipment image, wherein the processing make its determination of correct or incorrect set up by checking each segmented object, and wherein the transmitted data includes overlay image data for the AR headset to augment the scene by providing an indication of at least incorrectly set up segmented objects. The overlay image data may provide an indication also of correctly set up objects. The transmitted data may include an indication of any of the pre-defined objects that the computer apparatus was unable to segment from the equipment image.

In one example, the equipment set up involves arrangement of vials in set locations in relation to the equipment. The computer apparatus is configured to process the received scene image data to identify any vials found in the scene and to identify whether they are at their set locations. Making the determination of correct or incorrect equipment set up then takes account of whether the vials are at their set locations. The equipment set up may further involve arrangement of vials in relation to the equipment. The computer apparatus may then be further configured to process the received scene image data to perform vial identification on any vials found in the scene image data by reading a machine-readable code attached to any such vial. In response to the identification data is transmitted to the connected AR headset providing feedback information extracted through each code, e.g. as overlay image data, audio data, or a combination thereof.

In another example, the equipment set up involves removal of an item from the equipment. The computer apparatus is configured to segment the equipment image to identify whether the item has been removed or is still present, and wherein the transmitted data conveys an indication of a need for item removal. The transmitted data may include overlay image data for the AR headset to augment the scene by providing an indication of an item that is still in place.

In a still further example, the equipment set up involves correct operation of a spray nozzle. The computer apparatus is configured to receive scene image data from the connected AR headset of an image captured by the AR headset of a spray emission from the nozzle, e.g. by capturing an image of a test spray. The computer apparatus then performs image processing to assess whether the spray emission has a shape that falls within specification, e.g. a substantially conical shape within a specified range of solid angles.

The computer apparatus may be integrated with MBR/BR management software so that the equipment check is part of the operator actions specified in the MBR. Namely, the computer apparatus is configured to generate a BR during manufacture of the batch of pharmaceutical product by populating an MBR. The computer apparatus comprises: a process data structure defining a sequence of manufacturing process steps required to be carried out to manufacture a batch, the batch manufacturing process steps involving respective operator actions, and the manufacturing process steps including said one relating to the equipment set up; a mapping data structure that provides links between ones of the operator actions to ones of the content items and associated fields; an MBR comprising a plurality of content items and associated fields, wherein the fields are to be populated as an operator progresses through the operator actions. The computer apparatus is configured to: transmit overlay image data to the connected AR headset, the overlay image data presenting ones of the content items and associated fields to the operator in a way that follows the operator's progression through the operator actions as determined with reference to the mapping data structure and that is responsive to the operator populating the MBR fields; and populate fields of the MBR, as presented to the operator in the overlay image data, responsive to receipt of the user interface commands. A group of the operator actions relate to checking the equipment set up and linked thereto there is a group of content items and associated fields. The equipment set up checking process thus involves performing the operator actions and populating the associated MBR fields.

According to a further aspect of the disclosure there is provided a computer-implemented process for providing a process control function during manufacture of a batch of pharmaceutical product to check whether a piece of equipment has been set up correctly to carry out a manufacturing process step, the process comprising:

establishing a data communication connection between a computer apparatus and an augmented reality, AR, headset;

transmitting scene image data from the AR headset to the computer apparatus of an image captured by the AR headset;

processing the received scene image data by the computer apparatus to identify an image of the piece of equipment and making a determination of its correct or incorrect set up; and transmitting data from the computer apparatus to the connected AR headset conveying an indication of the correct or incorrect set up.

Another aspect of the disclosure provides a computer program product bearing machine-readable instructions for performing the computer-implemented process.

In summary, a computer-implemented process and computer apparatus for providing a process control function during manufacture of a batch of pharmaceutical product to check whether a piece of equipment has been correctly set up to carry out a manufacturing process step. An operator wearing an augmented reality, AR, headset captures a scene image of the equipment and transmits the image for processing. Based on the image processing a determination is made as to whether the piece of equipment has a correct or incorrect set up. Data is then transmitted to the AR headset conveying an indication of the correct or incorrect set up for the operator. The operator can then take appropriate remedial action before using the equipment to carry out a manufacturing step. The checking process can be integrated into an MBR and specifically a computer-implemented process for completing a BR from the MBR.

BRIEF DESCRIPTION OF THE DRAWINGS

This invention will now be further described, by way of example only, with reference to the accompanying drawings.

FIGS. 6A and 6B are simplified schematic representations of an MBR and a corresponding BR as used for documenting the manufacture of a batch of pharmaceutical product.

FIGS. 9 and 10 show by way of example sections of an example MBR.

FIGS. 11 and 12 show by way of example sections of an example MBR as marked up according to embodiments of the disclosure to highlight certain parts of the MBR.

FIGS. 14A and 14B show a checklist of components and reagents needed for a particular manufacturing step as may form part of an MBR and corresponding BR respectively.

FIGS. 15A and 15B show a list of pieces of equipment used during a batch manufacturing process as may form part of an MBR and corresponding BR respectively.

DETAILED DESCRIPTION

In the following detailed description, for purposes of explanation and not limitation, specific details are set forth in order to provide a better understanding of the present disclosure. It will be apparent to one skilled in the art that the present disclosure may be practiced in other embodiments that depart from these specific details.

Certain embodiments of the invention require an operator in a pharmaceutical manufacturing site to wear an AR headset. The AR headset may be in a glasses format (i.e. spectacles) or helmet and visor format, for example. An example AR headset that is commercially available is the Microsoft® Hololens®.

Figure 1:
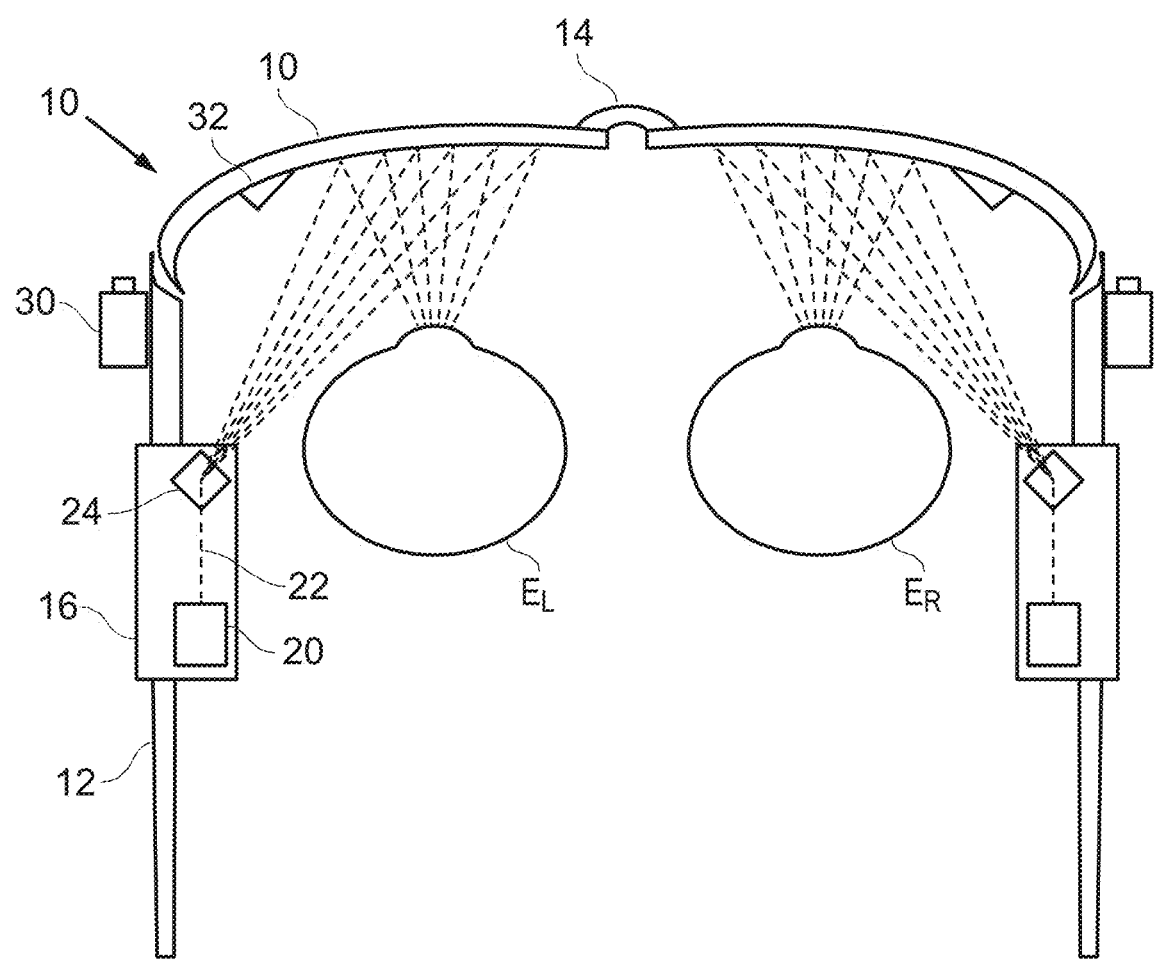
FIG. 1 schematically illustrates augmented reality glasses in a spectacles format.

FIG. 1 illustrates an example of an AR headset 1 in glasses format as it would be for a direct projection system in a spectacles format. The basic features in a spectacles format are a pair of lenses 10, a pair of temples 12 and a bridge 14. The AR headset 1 can be used to present an overlay image to a wearer. An overlay image may be an augmenting overlay image to augment the scene being viewed by the wearer, e.g. an arrow pointing to an object of interest in the scene as identified by image processing of video captured by a forward-facing camera. An overlay image may also be a non-augmenting overlay image that is intended to provide an image for the wearer to view that has no direct graphical link to the scene, e.g. to present a text-containing portion of a document for the wearer to read as a content item. The same image, or paired left- and right-hand image components, are directly projected onto the retinas of the wearer's left eye EL and right eye ER. With direct projection into both eyes it is possible not only to convey to the wearer conventional two-dimensional (2D) images, but also stereoscopic three-dimensional (3D) images. On each of the left and right sides, a housing 16 is integrated midway along a temple 12 and houses a light source unit 20. The light source unit 20 houses respective semiconductor laser diodes (LDs) or other suitable sources for emitting visible light in the red, green and blue (RGB) wavelength ranges respectively, thereby forming an RGB source module. The combined RGB light beam 22 output by the light source unit 20 is directed to a scanning element 24 which projects an image on the inside surface of the lens 10 on its side. In a direct retinal projection system, the inside surface of each lens 10 reflects the scanned beam onto a wearer's eyes EL and ER to directly project onto the wearer's retina. Alternatively, in other embodiments, the headset may use a conventional projection system, in which the wearer will view the image scanned onto the inside surface of the lenses 10. It will be understood that the reference to lenses does not imply that they have any lensing function insofar as the projection system is concerned, rather it merely follows conventional terminology. The lenses in the AR headset 1 have the primary function of enabling the overlay image to be displayed to the wearer by providing a reflection surface for direct retinal projection or a projection surface for conventional projection.

The AR glasses 1 include at least one forward-facing camera 30 operable to capture stills images or video in the field of view of the wearer. The mounting may be on the temple 12 as illustrated or may be integrated in the bridge 14 or rim (i.e. frame) around the lenses 10, for example. One or more wearer-facing cameras 32 may also be provided to capture images of the wearer's eyes, e.g. for eye tracking or eye segmentation. The mounting may be on the inner surface of the lenses 10 as illustrated or on the bridge 14, for example.

Figure 2:
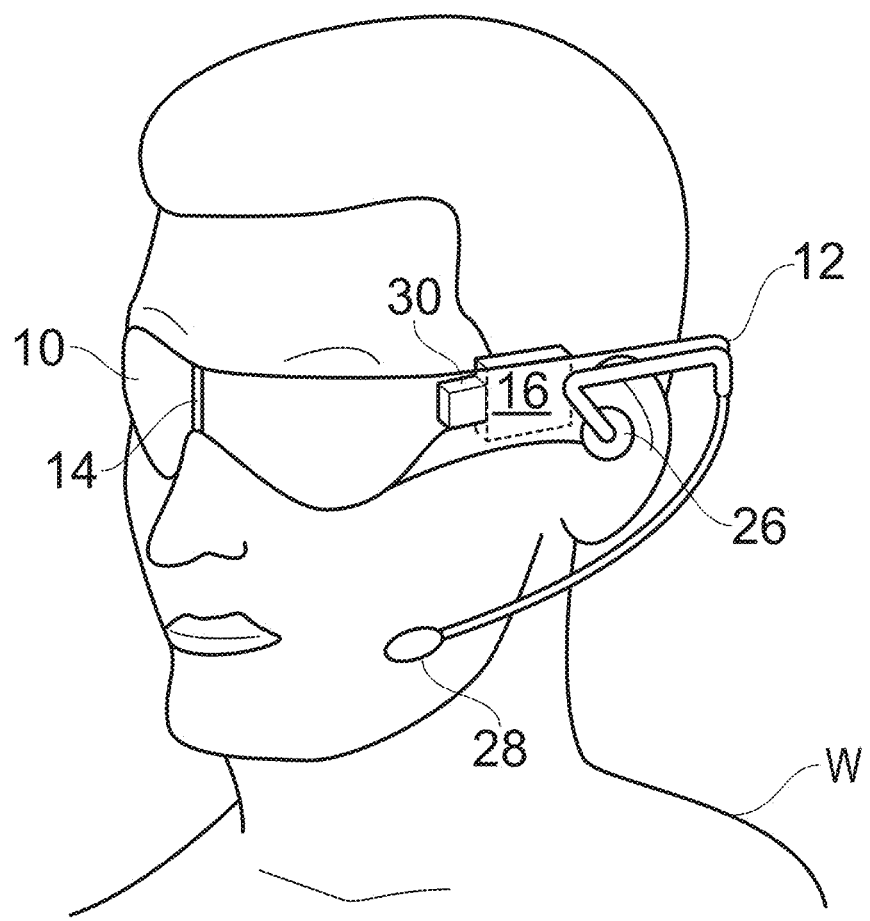
FIG. 2 is a schematic diagram of a person wearing the AR glasses of FIG. 1.

FIG. 2 is a schematic diagram of a wearer W wearing the AR glasses 1 of FIG. 1. In addition to the features visible in FIG. 1, there is shown an earpiece unit having an earpiece 26 arranged adjacent the wearer's ear canal for conveying an audio input to the wearer W as well as a microphone 28 arranged at the distal end of a supporting boom which may conveniently be attached to and formed integral with the earpiece unit.

The AR headset may have the following features:
- display (e.g. retinal or on inside surface of glasses)
- wireless (or wired) communication transceiver (e.g. via Bluetooth)
- forward-facing camera (for capturing gesture input, e.g. thumbs up for 'no', thumbs down for 'yes', diver-OK gesture for 'OK', sign language gestures, also for capturing images, e.g. of instrument or computer displays to collect individual numeric measurement values, graphs or whole or part of display screens as a screen capture)
- inward-facing camera (for eye-tracking, e.g. pupil tracking)
- microphone (audio in)
- speaker (audio out—typically headphone-type)
- touch sensor (for user input, e.g. through tapping or drag gestures)
- accelerometer (option for capturing gesture input, e.g. head shake for 'no' or nod for 'yes', tracking operator motion through the cleanroom optionally in combination with camera input
- gyroscope such as an optical fibre gyroscope (option to allow inertial tracking of an operator wearing the AR headset)
- sensors for monitoring the wearer or the wearer's environment (e.g. wearer's body temperature, carbon dioxide sensor to monitor wearer's tiredness, pulse sensor, humidity/dryness sensor to monitor air quality, radiation detector to measure wearer's accumulated exposure, sensor for any particular gaseous compound potentially associated with the manufacturing process, e.g. to sense if there is a leak of a hazardous compound)
- forward-facing directional temperature sensor, such as a thermal camera, to measure the temperature of objects of interest in the scene
- directional radiation detector which may be mounted on the AR headset or be provided as an ancillary hand-held component which can be pointed
- processor
- memory Some of these items, such as some of the sensors, may be present and in wireless or wired communication with the headset, but not integrated in the AR headset. For example, some sensors may be worn or carried by the operator.

The AR headset and optionally other ancillary devices may be collectively configured to provide a user interface (UI) for the wearer to interact with an application being run on a remote computer with a data communication link to the AR headset. The UI may use any combination of graphics on the AR headset, voice commands from the wearer, voice instructions to the wearer, handheld remote control with one or more buttons, e.g. in a button array, such as buttons for: scroll up, scroll down, field population with affirmative (tick), field population with negative (cross) etc. The UI may also enable the wearer to access training materials, which may be in document, audio or video form that are held in a central database that may also be co-hosted with the document management system. The pharmaceutical manufacturing process may be linked to the training materials, e.g. provide live training either mandated by the system or on demand by the wearer.

A user's input to a microphone, which will typically be integrated in the AR headset, may be in the form of natural language voice input which a processor in the AR headset or local thereto, or a processor remotely located, e.g. in the cloud, is operable to convert to text. For example, the user may have spoken to a virtual assistant (e.g. Apple Ski, Google Assistant, Microsoft Cortana-®s) running on a user equipment in possession of the wearer of the AR headset. The wearer is thus able to use natural language voice input to issue commands to the user interface. The UI may be provided with various commands linked to AR headset camera operation in order to capture stills or video images. One command may be to capture a stills image from the forward-facing camera of the AR headset and another command may be to capture a video clip from the same camera.

A video feed from a scene captured with a forward-facing camera of the AR headset may be image processed to perform segmentation and identify one or more objects of interest in the scene. The segmentation can be coordinated with the overlay projected onto the AR headset to augment the scene. Coordination can be aided by input from sensors on the AR headset and optionally also other sensors which indicate where the wearer is looking and how this is changes. The wearer's view direction or line of sight of the wearer can be tracked by one or more of the following sensor inputs: head motion tracking through a gyro and/or accelerometer; eye tracking; sensing the wearer's head position or body position. The wearer's position can be tracked by one or more of: following a tracking device worn by the user; following the user in the cleanroom through triangulated network of observation cameras of the type familiar from closed-circuit television (CCTV), which may for example be ceiling mounted; through inertial guidance with a gyro sensor. The image processing of image data input from an AR headset can be further aided by use of a 3D map of the cleanroom. The cleanroom may be mapped in detail, e.g. by architectural plans; through a triangulated network of observation cameras; through merging video feeds from the forward-facing cameras of AR headsets worn by people in the cleanroom; and by any combination of these. Segmentation may also be applied to a stills image, for example when a stills image forms part of a workflow for documenting completion of a task, e.g. completion of assembly of a unit.

Graphical overlays and other guidance and instructions given to the wearer may be delivered to the AR headset to guide an operator through a pharmaceutical manufacturing process. At the same time, process monitoring and compilation of documentation relating to the pharmaceutical manufacturing process can be supported by a combination of inputs received from the AR headset and from ancillary devices worn by the user. The AR headset cannot be used to guide and instruct, or monitor and document, it can involve the wearer in interactive operation so these actions merge. For example, if a known process is deviated from by the operator, the system can alert the operator via the AR headset, and then the operator is prompted to check his/her work and if needed take remedial action.

A forward-facing directional temperature sensor, such as a thermal camera, may be incorporated in the AR headset or an ancillary device, to capture a thermal map of the scene being viewed by the wearer. The thermal map may then be composited with the conventional scene. In this way, the temperature of objects of interest in the scene can be tracked. For example, if a chemical reaction that forms a step of the pharmaceutical manufacturing process is exothermic, and a particular temperature and/or temperature profile over time is associated with this reaction having been successful in the context of the manufacturing step, then this can be monitored and documented. Similarly, to thermal data, a directional radiation detector may be used to capture radioactivity type and level of radiopharmaceutical product or its precursors, and this may also be integrated into the segmented image of the scene.

Depending on the embodiment, not all of these features may be needed. At its most basic, the AR headset requires a display for visual display of text content from an electronic document in combination with a user interface to allow the operator to make entries into an electronic document and an appropriate communication channel to transfer data to and from the AR headset to a computer system that manages the electronic documents.

Figure 3:
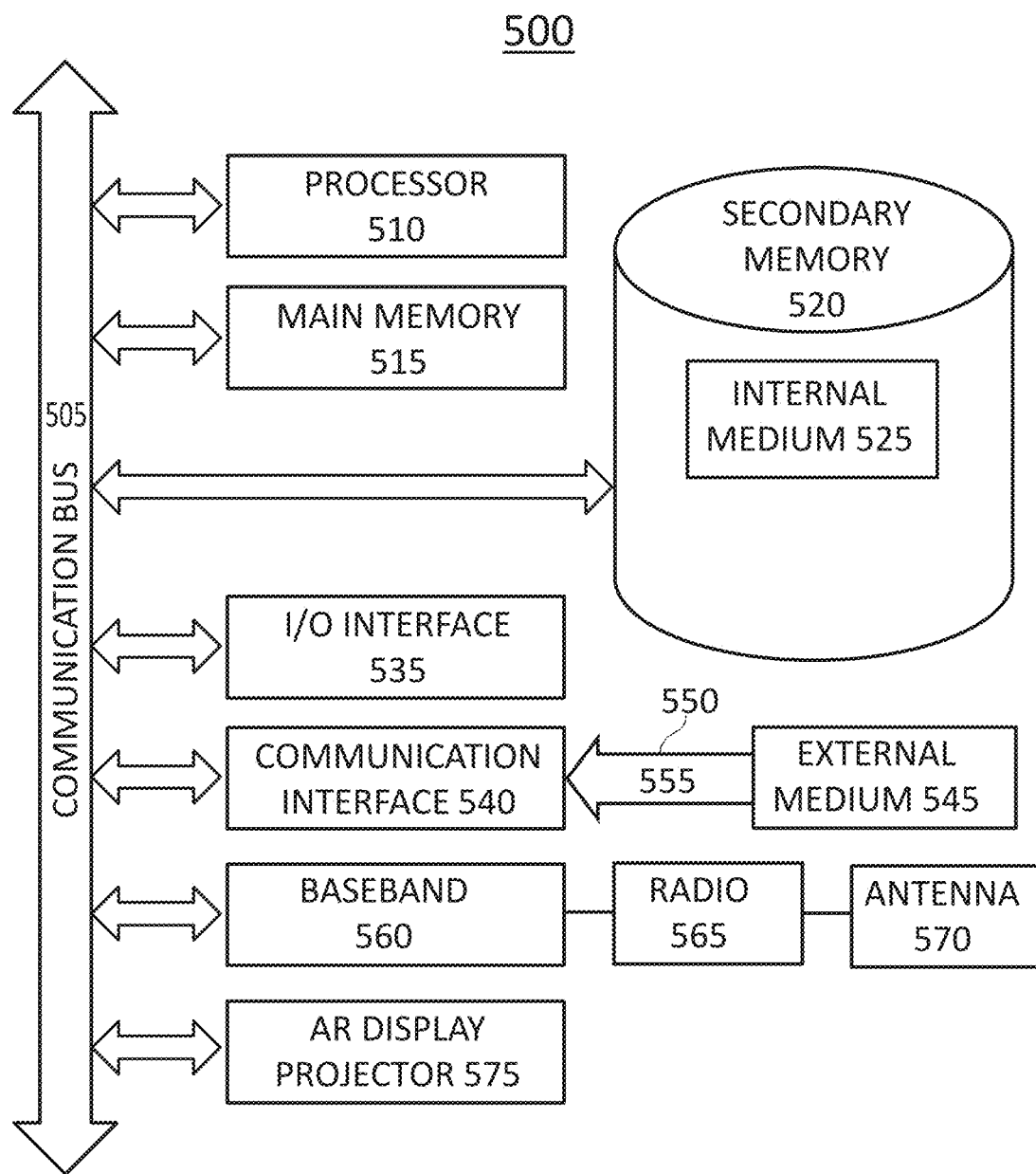
FIG. 3 is a block schematic diagram of a generic computing apparatus as may be integrated into the AR glasses of FIG. 1 or used in conjunction therewith.

FIG. 3 is a block schematic diagram of a computing apparatus 500 such as may be integrated into the AR headset of FIG. 1 or used locally to the headset wearer in conjunction therewith, e.g. via a local wireless or wired communication connection. The associated electronic components may also be accommodated in the housing 16 or may be arranged in some local ancillary component worn or carried by the wearer, e.g. a collar yoke, utility belt, helmet, pocket format unit placed, e.g. in a vest. The local computing apparatus 500 can provide limited capabilities for image and other data processing, data storage and so forth, so that the AR headset 1 may act, for example, as: a thin client to reproduce images received via its transceiver, initial processing of a wearer's graphical UI (GUI) actions such as gestures or eye tracking.

The computing apparatus 500 can be any processor-enabled device that is capable of wired or wireless data communication. Other computing apparatus, systems and/or architectures may be also used. Computing apparatus 500 preferably includes one or more processors, such as processor 510. The processor 510 may be for example a central processing unit (CPU), graphics processing unit (GPU), tensor processing unit (TPU) or arrays or combinations thereof such as CPU and TPU combinations or CPU and GPU combinations. Additional processors may be provided, such as an auxiliary processor to manage input/output, an auxiliary processor to perform floating point mathematical operations (e.g. a TPU), a special-purpose microprocessor having an architecture suitable for fast execution of signal processing algorithms (e.g., digital signal processor, image processor), a slave processor subordinate to the main processing system (e.g., back-end processor), an additional microprocessor or controller for dual or multiple processor systems, or a coprocessor. Such auxiliary processors may be discrete processors or may be integrated with the processor 510. The processor 510 is connected to a communication bus 505. Communication bus 505 may include a data channel for facilitating information transfer between storage and other peripheral components of computing apparatus 500. Communication bus 505 further may provide a set of signals used for communication with processor 510, including a data bus, address bus, and control bus (not shown). The computing apparatus 500 preferably includes a main memory 515 and may also include a secondary memory 520. Main memory 515 provides storage of instructions and data for programs executing on processor 510, such as one or more of the functions and/or modules discussed above. Main memory 515 is typically semiconductor-based memory such as dynamic random access memory (DRAM) and/or static random access memory (SRAM). The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). Secondary memory 520 may optionally include an internal memory 525. The secondary memory 520 may include other similar elements for allowing computer programs or other data or instructions to be loaded into computing apparatus 500. Such means may include, for example, an external storage medium 545 and a communication interface 540, which allows software and data to be transferred from external storage medium 545 to computing apparatus 500.

As mentioned above, computing apparatus 500 may include a communication interface 540. Communication interface 540 allows software and data to be transferred between computing apparatus 500 and external devices which may be networked together. For example, computer software or executable code may be transferred to computing apparatus 500 from a network server via communication interface 540. The communication interface 540 preferably implements industry-promulgated protocol standards, such as Ethernet IEEE 802 standards, fibre channel, digital subscriber line (DSL), asynchronous digital subscriber line (ADSL), frame relay, asynchronous transfer mode (ATM), integrated digital services network (ISDN), personal communications services (PCS), transmission control protocol/Internet protocol (TCP/IP), serial line Internet protocol/point to point protocol (SLIP/PPP), and so on, but may also implement customised or non-standard interface protocols as well. Software and data transferred via communication interface 540 are generally in the form of electrical communication signals 555. These signals 555 may be provided to communication interface 540 via a communication channel 550. In an embodiment, communication channel 550 may be a wired or wireless network, or any variety of other communication links. Communication channel 550 carries signals 555 and can be implemented using a variety of wired or wireless communication means including wire or cable, fibre optics, conventional phone line, cellular phone link, wireless data communication link, radio frequency (RF) link, or infrared link, just to name a few. Computer-executable code (i.e., computer programs or software) is stored in main memory 515 and/or the secondary memory 520. Computer programs can also be received via communication interface 540 and stored in main memory 515 and/or secondary memory 520. Such computer programs, when executed, enable computing apparatus 500 to perform the various functions of the disclosed embodiments as described elsewhere herein.

In this document, the term "computer-readable medium" is used to refer to any non-transitory computer-readable storage media used to provide computer-executable code (e.g., software and computer programs) to computing apparatus 500. Examples of such media include main memory 515, secondary memory 520 (including internal memory 525 and external storage medium 545), and any peripheral device communicatively coupled with communication interface 540 (including a network information server or other network device). These non-transitory computer-readable media are means for providing executable code, programming instructions, and software to computing apparatus 500. In an embodiment that is implemented using software, the software may be stored on a computer-readable medium and loaded into computing apparatus 500 by way of input/output (I/O) interface 535, or communication interface 540. In such an embodiment, the software is loaded into computing apparatus 500 in the form of electrical communication signals 555. The software, when executed by processor 510, preferably causes processor 510 to perform the features and functions described elsewhere herein.

The I/O interface 535 provides an interface between one or more components of computing apparatus 500 and one or more input and/or output devices. Example input devices include the forward-facing camera(s) 30, the eye-directed camera(s) 32, audio in/out, accelerometer, gyroscope, sensors etc. and any other inputs associated specifically with the AR headset as well any other sensors or standard UI devices such as keyboards, touch screens or other touch-sensitive devices, biometric sensing devices, computer mice, trackballs, pen-based pointing devices, and the like.

The computing apparatus 500 also includes optional wireless communication components that facilitate wireless communication over a voice network and/or a data network. The wireless communication components comprise an antenna system 570, a transceiver radio system 565, and a baseband system 560. In computing apparatus 500, RF signals are transmitted and received over the air by antenna system 570 under the management of the transceiver radio system 565. The antenna system 570 may comprise one or more antennae and one or more multiplexors (not shown) that perform a switching function to provide antenna system 570 with transmit and receive signal paths. In the receive path, received RF signals can be coupled from a multiplexor to a low noise amplifier (not shown) that amplifies the received RF signal and sends the amplified signal to the transceiver radio system 565. The transceiver radio system 565 may comprise one or more transceivers that are configured to communicate over various frequencies. The radio system 565 combines a demodulator (not shown) and modulator (not shown) for receiving and transmitting respectively, which may be implemented in one integrated circuit (IC) or separate ICs. In the incoming path, the demodulator strips away the RF carrier signal leaving a baseband receive audio signal, which is sent from radio system 565 to baseband system 560. The baseband system 560 is also communicatively coupled with processor 510, which may be a CPU. Processor 510 has access to data storage areas 515 and 520. Processor 510 is preferably configured to execute instructions (i.e., computer programs or software) that can be stored in main memory 515 or secondary memory 520. Computer programs can also be received from baseband processor 560 and stored in main memory 510 or in secondary memory 520 or executed upon receipt. Such computer programs, when executed, enable computing apparatus 500 to perform the various functions of the disclosed embodiments. For example, data storage areas 515 or 520 may include various software modules.

The computing apparatus is shown integrated with an AR display projector 575 integrated with the light sources 20 and directly attached to the communication bus 505.

The data processed locally, i.e. in the AR headset or with an ancillary computer apparatus local to the wearer, may include data captured from devices and sensors integrated with the AR headset for onward transmission to the network or internal local processing by the AR headset and data received by the AR headset from the network for communication to the wearer. The data may be acquired and/or processed remotely at a computing node located at an arbitrary location in the network. The local computer apparatus may be operatively coupled to any remote computing nodes or data storage by communication links, such as via wired or wireless communication links. The wearer-facing camera(s) can be used to capture eye images for eye image segmentation or eye tracking.

A remote computing node may be configured to analyse and process data and/or image information such as stills images and video images captured by the AR headset's camera(s). Captured image data may be stored locally for a limited amount of time, e.g. until safely transmitted onward or for the duration of a shift or user session. In some embodiments, there may be a remote digital data storage device, which may be available through the internet or other networking configuration in a "cloud" resource configuration.

Various embodiments may also be implemented primarily in hardware using, for example, components such as application specific integrated circuits (ASICs), programmable logic arrays (PLA), or field programmable gate arrays (FPGAs). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system.

Skilled persons can implement the described functionality in varying ways for each particular application, but such implementation decisions should not be interpreted as causing a departure from the scope of the invention. In addition, the grouping of functions within a module, block, circuit, or step is for ease of description. Specific functions or steps can be moved from one module, block, or circuit to another without departing from the invention.

Moreover, the various illustrative logical blocks, modules, functions, and methods described in connection with the embodiments disclosed herein can be implemented or performed with a general purpose processor, a digital signal processor (DSP), an ASIC, FPGA, or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, read-only memory (ROM) memory, erasable programmable ROM (EPROM) memory, electrically erasable PROM (EEPROM) memory, registers, hard disk, a removable disk or any other form of storage medium including a network storage medium. An exemplary storage medium can be coupled to the processor such that the processor can read information from, and write information to, the storage medium. In the alternative, the storage medium can be integral to the processor. The processor and the storage medium can also reside in an ASIC.

A computer readable storage medium, as referred to herein, is not to be construed as being transitory signals per se, such as radio waves or other freely propagating electromagnetic waves, electromagnetic waves propagating through a waveguide or other transmission media (e.g., light pulses passing through a fibre-optic cable), or electrical signals transmitted through a wire.

Any of the software components described herein may take a variety of forms. For example, a component may be a stand-alone software package, or it may be a software package incorporated as a "tool" in a larger software product. It may be downloadable from a network, for example, a website, as a stand-alone product or as an add-in package for installation in an existing software application. It may also be available as a client-server software application, as a web-enabled software application, and/or as a mobile application.

Embodiments of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

The computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Figure 4:
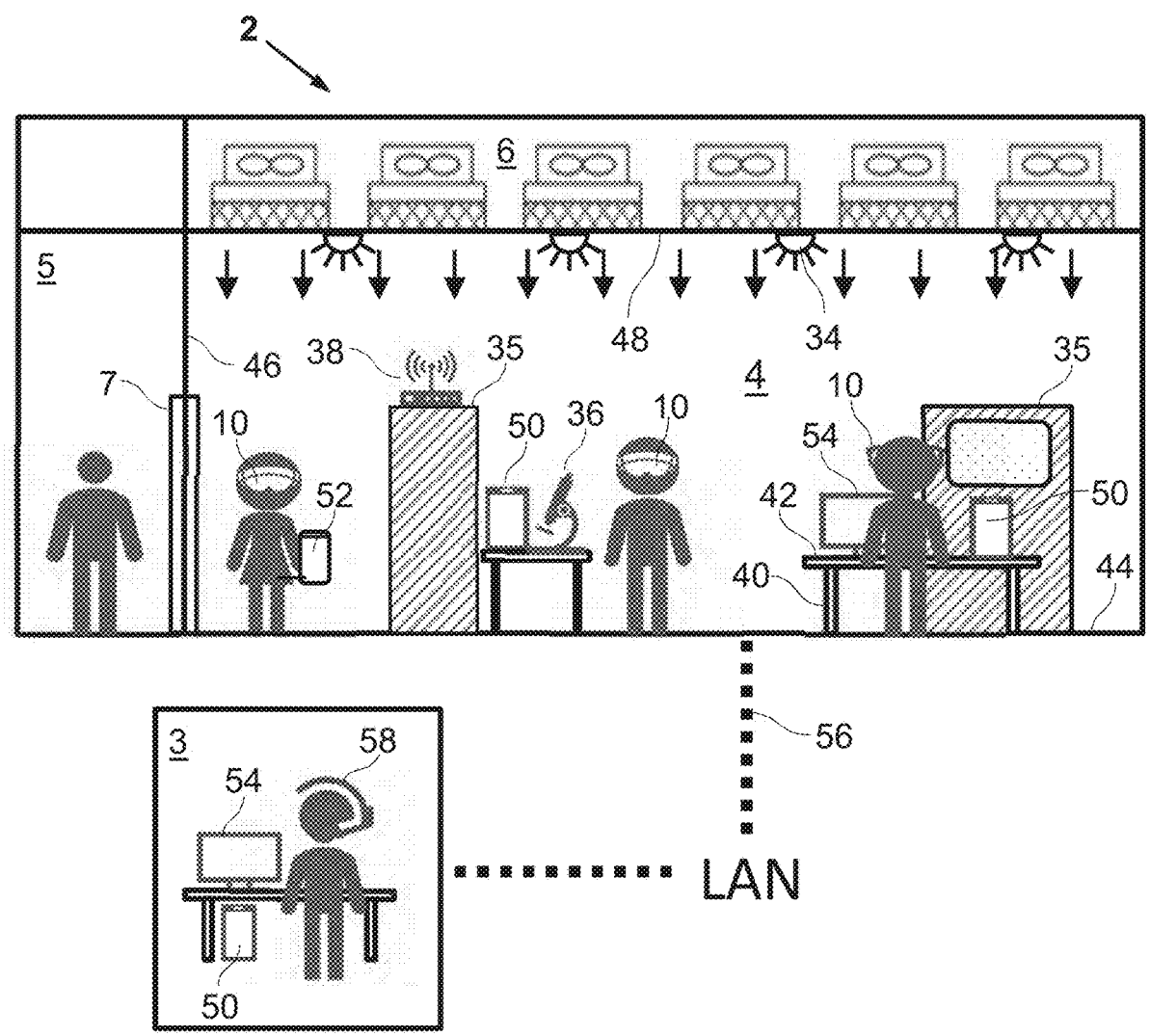
FIG. 4 is a schematic drawing of a clean room of a pharmaceutical manufacturing site and an office in the site.

FIG. 4 is a schematic drawing of a clean room 2 of a pharmaceutical manufacturing site or facility and an office 3 in the same site, where the computer equipment in the clean room 2 and the office 3 are in wireless or wired communication with each other through a common LAN. Alternatively, the office 3 could be at a remote location, in which case a WAN possibly including cloud components would be involved in connecting the office 3 to the clean room 2. The cleanroom 2 is shown with a clean area 4, an air lock and gowning area 5, the two being interconnected by an access door 7, and a ceiling duct area 6 where banks of filters are arranged. In the clean area 4, there are various pieces of manufacturing equipment 35 and instrumentation 36 as well as associated computer apparatus 50 and displays 54. A wireless router 38 is also shown which may enable various wireless-network enabled devices to communicate with each other and also to communicate externally, for example with network-enabled devices in the office 3 via a network connection 56 that provides a data communication channel between network nodes. The operators may also use handheld computer apparatuses 52 such as tablets or mobile phones. The clean area 4 also contains pieces of furniture 40, such as tables and cabinets, with surfaces 42 which may need to be cleaned as part of any cleaning protocol, e.g. together with the floor surfaces 44, wall surfaces 46 and/or ceiling surfaces 48. A triangulated network of static observation cameras 34 of the type familiar from CCTV are provided, whose fields of view overlap to allow for reliable tracking and hand-over between cameras, as may be provided for by wide-angle lenses. The observation cameras 34 are operable to support mapping of the cleanroom and tracking of the movement of operators, portable equipment and pharmaceutical product. The observation cameras 34 may be predominantly ceiling mounted as schematically illustrated or also mounted elsewhere as needed to provide complete coverage of the cleanroom. The office 3 is for a supervisor to monitor, audit and make release decisions in relation to the pharmaceutical manufacturing. The office 3 contains suitable computer equipment to allow a supervisor to complete these tasks. By way of example, we illustrate a computer apparatus 50, display 54 and headset 58 being worn by the supervisor. The headset may be an AR headset, but could also be a conventional headset consisting only of audio in/out channels, in which case the supervisor would rely on the display 54 for viewing image data.

Figure 5:
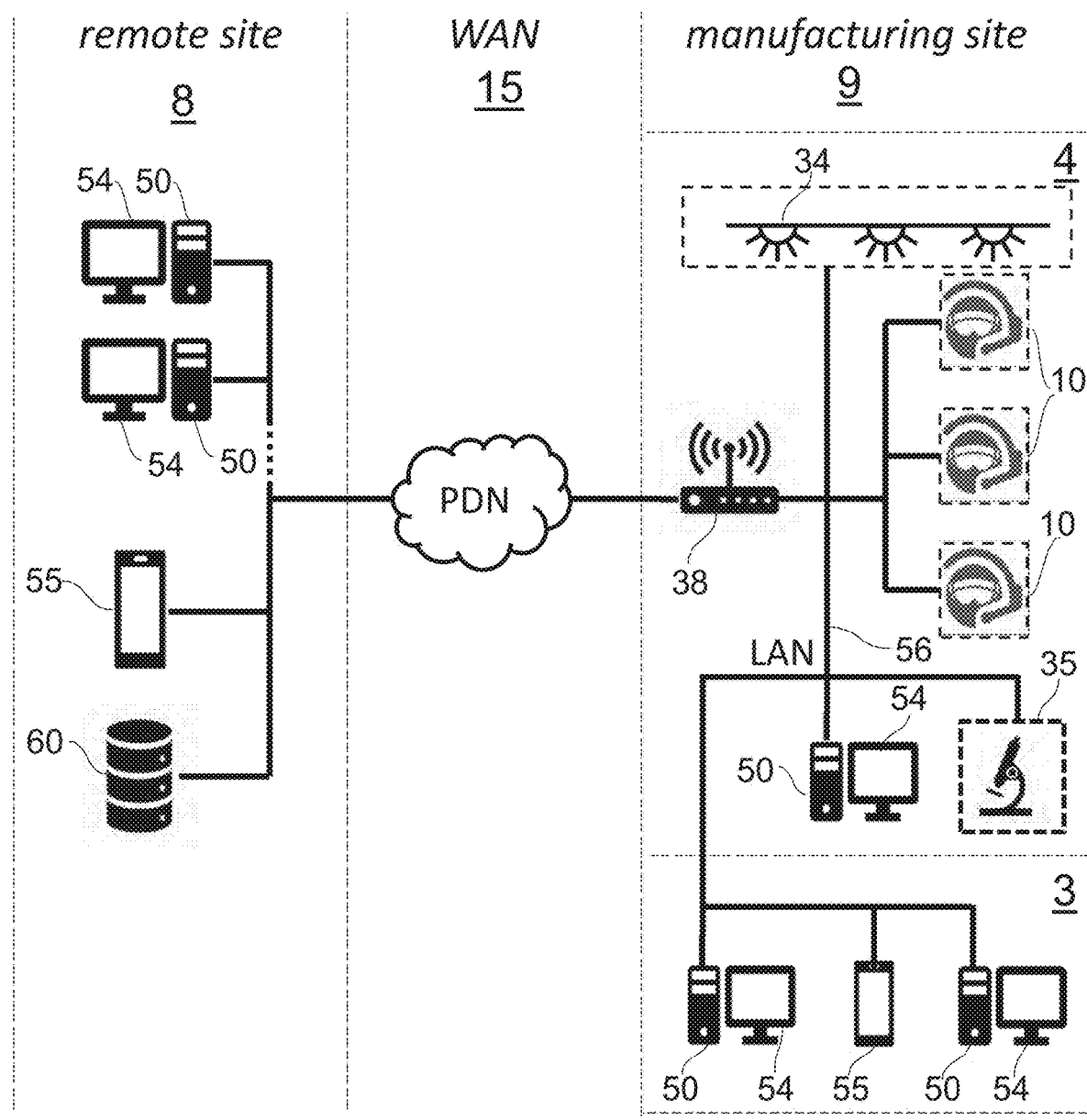
FIG. 5 is a schematic drawing of an example computer network including network nodes located in the cleanroom and in the office of a pharmaceutical manufacturing site as shown in FIG. 4 as well at a remote site.

FIG. 5 is a schematic drawing of an example computer network including network nodes located in the cleanroom 4 and in an office 3 of a pharmaceutical manufacturing site 9 as shown in FIG. 4 as well at a remote site 8. The remote site 8 is connected to the manufacturing site 9 via a WAN connection 15 which may be a packet data network (PDN). The WAN may include telecommunication components such as in a long-term evolution (LTE) 5G network, cloud computing components and/or point-to-point secure connections. As well as the components already described, which are labelled with the same reference numerals, there is additionally shown servers 55 and a database 60. The servers may host data storage, which may be virtualised. The database 60 is shown at the remote site 8. A database may also be provided at the manufacturing site. Multiple databases may exist at each site. Moreover, the databases and other data repositories at the remote and manufacturing sites 8, 9 may be duplicates that are mirrored to each other, either in their live state, or with backups. The network may at least in part incorporate a laboratory information management system (LIMS). The manufacturing site may be a radiopharmaceutical manufacturing site which serves one or more hospitals. The network may therefore be integrated with or be linked to a larger clinical network environment, such as a hospital information system (HIS) or picture archiving and communication system (PACS). At least some of the data used by or generated by the manufacturing site may include patient data, which may be retained in a patient information database containing the electronic medical records of individual patients. Barcode labels may be used in the manufacturing process, e.g. to label reagents, components such as filters or single-use plastics items, and batches of pharmaceutical product, by which the barcoded items are tagged with metadata. The AR headsets may incorporate local hardware and/or software to provide a barcode reading functionality. The image capture for the barcode reader may be through a general-purpose forward-facing camera on the AR headset or a specialist handheld unit available to the operator.

A cloud computing environment may be used to host and deliver one or more of the units at the network nodes shown in FIG. 5, for example one or more of the above-mentioned servers and databases. Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models. Broad network access may be used to provision the cloud-hosted services over the network and may be accessed through standard mechanisms that promote use by heterogeneous thin or thick client platforms (e.g. personal computers, tablets, mobile phones, laptops). The favoured deployment model for pharmaceutical manufacturing is a private cloud in which the cloud infrastructure is operated solely for an organisation. It may be managed by the organisation or a third party and may exist on-premises or off-premises. A cloud computing environment is service oriented with a focus on statelessness, low coupling, modularity, and semantic interoperability. At the heart of cloud computing is an infrastructure that includes a network of interconnected nodes.

Manufacturing of pharmaceuticals is performed according to and controlled by formal regulations, instructing the operator on how to perform the tasks which collectively implement the chemical and physical steps leading to a finished pharmaceutical product. Such regulations are usually complied with through a Master Batch Record (MBR), a document generated by the holder of the Marketing Authorisation (MA) or the sponsor of a study to ensure compliance with established procedures, granted marketing approvals and sometimes also intellectual property licenses. Completion of an MBR during manufacturing of a batch is akin to filling out a complicated form full of check boxes and other entries. A completed MBR is referred to as a batch record (BR), i.e. a BR is a completed MBR for a specific batch. The BR has the role of documenting the full process from preparatory work via the setup of the campaign, the execution of the process, equipment cleaning procedures between batches or during a batch and dispensing procedures. The batch manufacturing process steps will typically comprise a mixture of chemical and physical process steps and verification steps for quality control, such as taking measurements. The measurements may include chromatographic or spectroscopic measurements or other complex analyses with specialist instruments. The measurements may also include basic physical parameter measurements such as of weight, volume, temperature, pressure or radioactivity level.

Figures 6A, 6B:
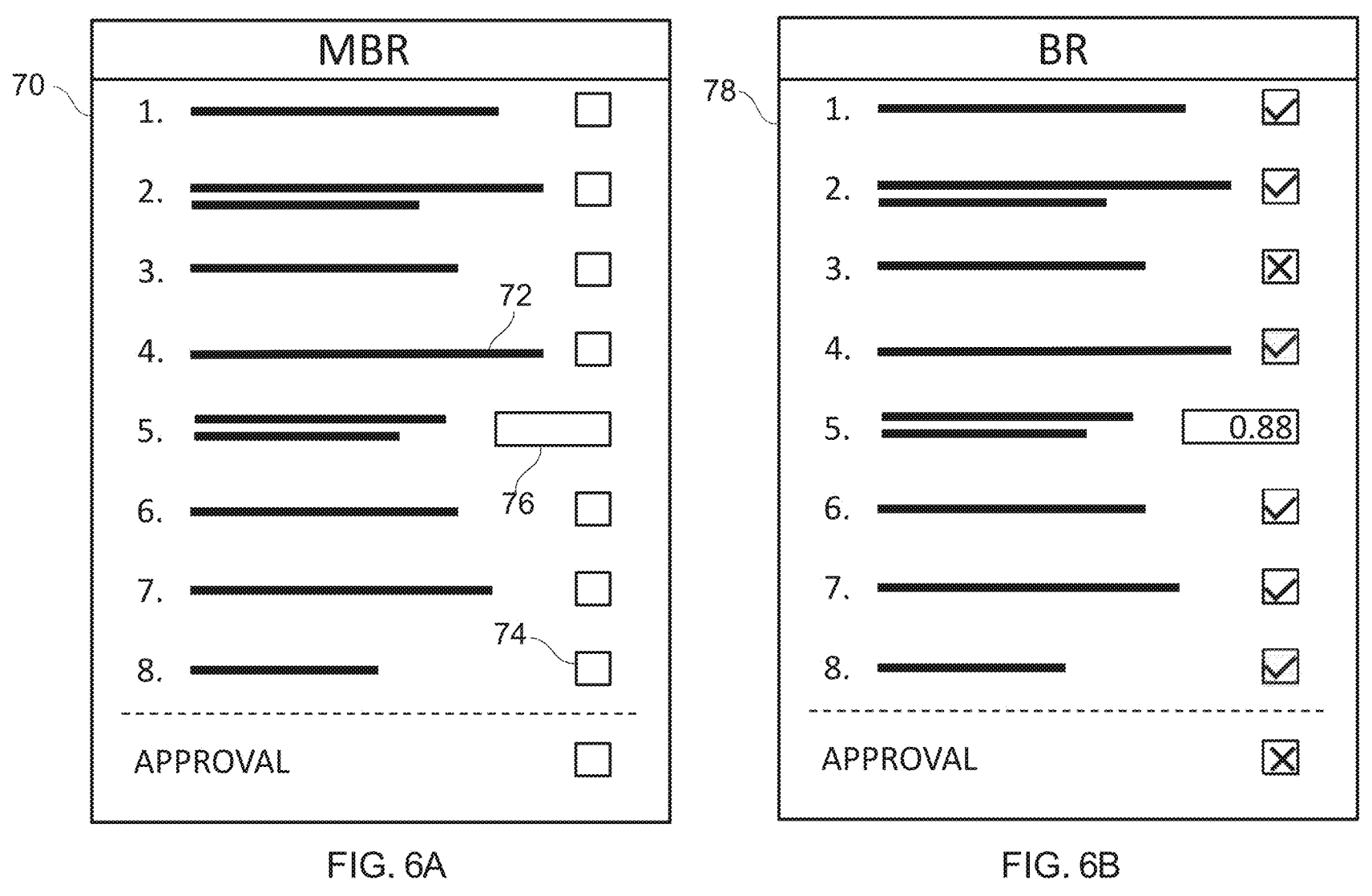

FIGS. 6A and 6B are simplified schematic representation of an MBR and a corresponding BR. An MBR is a document of key significance for manufacturing pharmaceutical products. The MBR is generated by the holder of the MA for the pharmaceutical product, or the sponsor of a study, to ensure compliance with established procedures, granted marketing approvals and sometimes also intellectual property licenses. The MBR serves as a template or form which is required to be completed or filled in when a batch of the pharmaceutical product is manufactured in order to document that the batch complies with what is specified in the MA and any other factors imposed by the originator of the MBR to certify that the batch is compliant with required practice. FIG. 6A is a simplified schematic representation of one part of an MBR 70 which comprises a sequential list of tasks (i.e. operator actions), labelled 1 to 8, each task carrying a descriptor 72, typically in text form, but possibly including some graphics elements, and a field 74, 76 for completion. The descriptor is thus a content item in the MBR relating to a specific one of the operator tasks or actions that alone or collectively with other operator tasks form a process step. Some fields may be check boxes 74 whereas other fields 76 may require entry of another variable type, such as a floating point or integer value relating to a measurement parameter such as a temperature, a weight or the number of units of a discrete item. There may also be a check box for approval after a sequence of tasks, which may relate to one step in the manufacturing process, e.g. that involved tasks 1-8 as illustrated, or may be for the whole manufacturing process after all the MBR has been worked through to create a completed BR. FIG. 6B shows a corresponding BR 78 in which the fields have been populated. By way of example, task 3 was not successfully completed as indicated by the cross, whereas the other tasks 1, 2, 4, 6, 7, 8 were successfully completed as indicated by the tick (check). In addition, an entry of 0.88 was made in the numeric field for task 5. A scalar quantity will be checked to see if it lies within a permitted range, whereas an integer quantity may either be specified in terms of a range of integer values or may require an exact integer value to be met. As a result of the unsuccessful completion of task 3, the approval check box is also crossed.

The fields in the BR are populated in embodiments of the invention by a combination of operator actions through the UI of the AR headset and automatic population through data logging performed as supported by the AR headset, e.g. through image processing of images captured by the AR headset. The UI of the AR headset has a GUI component which is configured to cooperate with non-augmenting overlay image data relating to the content of the MBR, whereby a plurality of user command inputs are provided which collectively enable the operator to navigate between fields of the MBR contained in the overlay image data being displayed and to populate the MBR fields with the appropriate entries. The UI thus allows the operator to work through completion of the BR in a stepwise manner. One UI command may be a confirmation command to populate a field 74 with an affirmation of task completion. The field 74 is envisaged to be associated with a discrete valued parameter. Such a field may for example be binary (e.g. not yet done/done) or may be tri-state (e.g. not yet done, successfully done, unsuccessfully done). Another UI command may be a numeric value entry command to populate a field 76 with a number.

Figure 7:
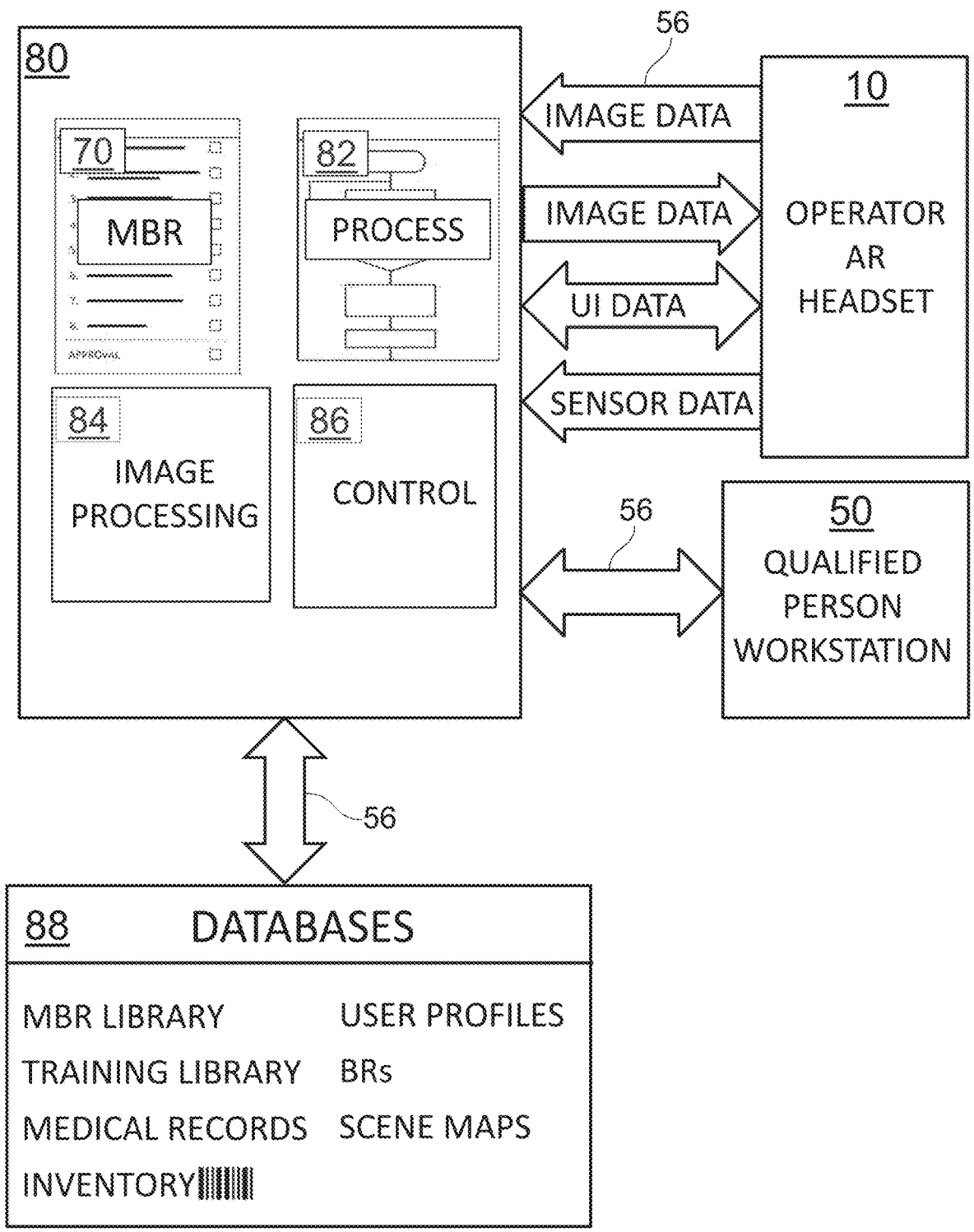
FIG. 7 is a block diagram of applications, data structures and functional units hosted by the computer network of FIG. 5.

FIG. 7 is a block diagram of applications, data structures and functional units hosted by the computer network of FIG. 5. A computer application 80 is hosted by and run on a server as shown in FIG. 5. The computer application 80 provides electronic record management system software for an MBR 70, e.g. batch record management system software for managing the MBR and the BR. To manufacture a pharmaceutical product of interest, the relevant MBR is loaded into the computer application 80. The manufacturing process underlying the pharmaceutical product manufacture is defined in a data structure 82 which is a process flow with sequences of tasks, conditional branches and so forth which is also loaded in the computer application 80. Embedded in the data structure of the process flow are mappings between, including time synchronisations, between populating the MBR fields in the data logging steps and undertaking the operator actions according to the process flow. Embedded in the data structure of the process flow or as tags added to the MBR are also criticality gradings for the operator tasks in the MBR. The gradings may have two or more levels, e.g. 3 or 4 levels. When generating a non-augmented overlay image for an AR headset to display content (e.g. descriptor and field) for a particular task, the criticality grading can be used to modify how said content is rendered on the display apparatus. Visually perceptible markings on task-specific content can be used to distinguish between content having regard to the criticality grading associated with the task, e.g. with highlighting and/or a colour scheme and/or use of bold type or underlining in order that more critical tasks are emphasised to the operator.

The computer application 80 also includes a diverse suite of image processing functionalities 84 to support interaction of the computer application 80 with an AR headset 10 being worn by an operator as well as with a workstation 50 for a qualified person (QP) responsible for approvals and ultimate batch release. These image processing functionalities are described in more detail further below. The computer application 80 further includes a control module 86 which has the function of coordinating the other elements 70, 82, 84 of the computer application 80 with the external components associated with operators, QPs and database read and write actions, including taking account of the mappings in the process flow to synchronize with stepping through the MBR fields. The computer application 80 is configured to generate overlay image data relating to tasks selected from the MBR in synchronisation with progression of the operator through these tasks. For this purpose, the computer application causes suitable overlay image data to be loaded onto the AR headset for the operator. The overlay images may be a combination of augmenting and non-augmenting overlay images.

The computer application 80 and its underlying host computer system, e.g. 55, being in operative communication with the AR headset 10 via data communication channel, e.g. 56. FIG. 7 shows schematically some of the more important data communication functions carried out between the computer application 80 and the AR headsets 10 being used by operators in the cleanroom. Image data is sent to the AR headset for display to the wearer through the display apparatus. Image data is sent from the AR headset as output from the camera(s) mounted on the AR headset. UI data passes both ways between the computer application and the AR headset. Sensor data passes from the AR headset (or from ancillary devices) to the computer application. The computer application 80 also has access to a suite of databases 88 via a data communication channel 56. The databases are schematically shown in a single functional bloc, but each of the listed items will usually be in an independent database which may be hosted in different physical servers or virtual servers, e.g. 60, or share storage resource, or be combined into a single database. The listed databases are as follows.

There is a library of MBRs, one for each pharmaceutical product that may be manufactured in a particular manufacturing site or any manufacturing site of an entity with multiple manufacturing sites.

There is a training library where units of training materials are stored. The training units may be based on multimedia content including one or more of video clips, individual stills images, sequences of stills images, e.g. in comic-book format, audio and text. Each training unit may be associated with a specific operator action (task) or group of operator actions (process step). Metadata tagged to the MBR 70 or embedded in the process data structure 82 or contained in the control module 86 may link to specific training units, so that the computer application 80 when run is operable to play training units on the AR headset selected in synchronisation with progression through the operator actions and optionally other factors such as with reference to the user profile of the operator.

The training units include metadata enabling a training management algorithm to decide at run time whether that training unit should be offered or mandated (for example with reference to the operator profile, or the mode of operation, e.g. training mode or manufacturing mode, or responsive to the actual operator actions that are being carried out, e.g. if the operator has spent too long on an action or group of actions that may be taken as an indicator that the operator needs assistance).

The AR headset's UI may be provided with user commands to enable non-mandatory training units to be offered to the operator and to be accepted or refused by the operator by issuing these commands.

The control module 86 may also support an operator training mode which includes enhanced use of the training units from the training library. The training mode may additionally make use of an operator scoring unit in which metrics logging performance of an operator are collected and which is configured to provide pass/fail gradings of a manufacturing process, or a group of operator actions within a manufacturing process, on which the operator is being trained.

There may be a medical records database holding patient data. This may be remotely hosted on a different site, e.g. as part of a PACS hospital network, but may allow controlled access to the computer application, if only to allow, for example, ordering information from patient records to be accessed by the computer application, so that the computer application can collect orders, e.g. to manufacture a batch of radiopharmaceutical product for all patients scheduled for a particular type of scan on that day.

There is an inventory database for all raw materials, such as reagents, and also for batches of finished or semi-finished pharmaceutical products, and any other items that need to be tracked, e.g. waste vials. Tracking is conventionally done through barcodes. The inventory database may therefore provide a lookup facility for a barcode reader. For example, each reagent vial, waste vial, and product vial may be labelled with a barcode. Consumable items, such as well plates and microscope slides may also be barcoded. The barcode scanning may be integrated in the AR headset using the forward-facing camera or done with a separate barcode reader. Metadata associated with the barcode is held in the inventory database, such as nature of product, expiry date/time of product, manufacturer/supplier of a raw material etc.

There is another database for user profiles. For example, there may be standard user profiles for different types of worker, such as for an operator who works in the cleanroom to perform manufacturing tasks (e.g. subdivided as trainee, regular, expert/supervisor) and for a QP responsible for approvals and ultimate batch release (e.g. subdivided by approval authorisation grade). In addition, the user profiles may be personalised so that each individual staff member has his/her own profile. An operator profile may then be personalised by factors such as operator skill, operator track-record (e.g. as measured by performance metrics such as speed and reliability), operator training modules that have been completed.

When generating the above-mentioned non-augmented overlay image for an AR headset to display content (e.g. descriptor and field) for a particular task, how said content is rendered on the display apparatus can be modified not only having regard to the criticality grading, but also having regard to the combination of criticality grading and user profile, e.g. to take account of operator skill attributes and/or operator track-record as stored in the user profile. For example, the system may largely refrain from any highlighting of tasks for an expert operator. On the other hand, if a personalised user profile shows that a particular operator has a track-record of unreliability with a particular task, then this can be highlighted even if it would not be for a regular operator with a similar general skill level.

The BRs of manufactured batches are also stored in a database.

A scene map database is also provided to store 3D maps (or perhaps only 2D plan view maps) of each of a plurality of cleanrooms. The cleanrooms may be mapped in detail, e.g. by architectural plans; through a triangulated network of observation cameras; through merging video feeds from the forward-facing cameras of AR headsets worn by people in the cleanroom; and by any combination of these. The cleanroom maps can then be accessed to merge video or still image capture from AR headsets, e.g. to present accurate overlays on the AR headset. With reference to the map and tracking of an operator's position within the cleanroom, it is possible to use a volume renderer to establish the view point and view axis of the operator. A cleanroom map may also be used to direct an operator to the location where the next task is to be completed, to cause capture of a stills image or video clip automatically, i.e. without operator input, but rather triggered by the control module 86.

It will be understood that any combination of these databases may be provided and also additional databases may be provided.

Figure 8:
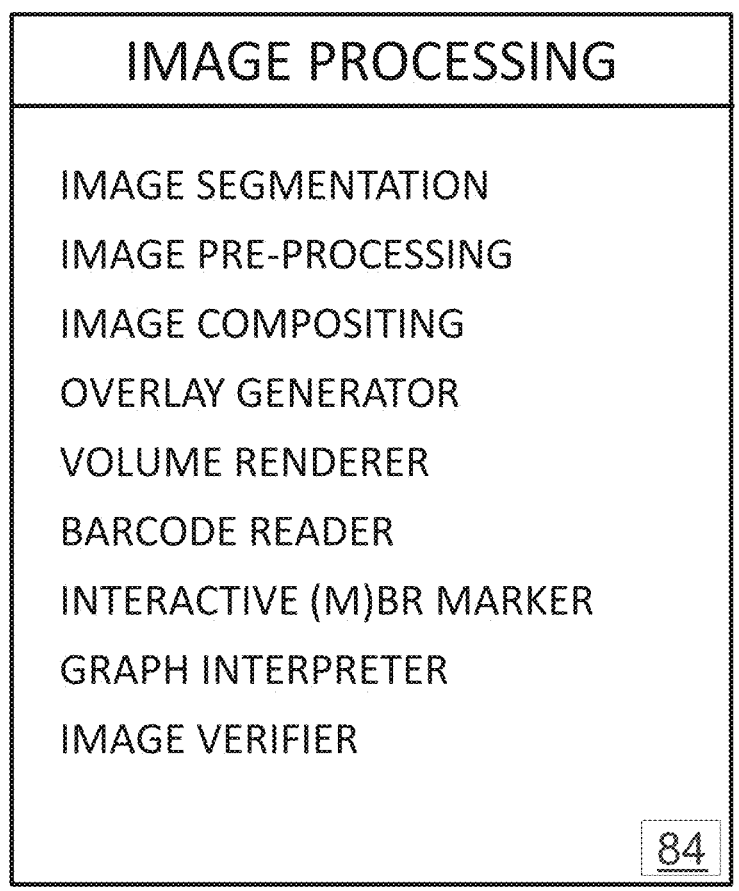
FIG. 8 shows example functional units for image processing.

FIG. 8 shows example functional units for image processing.

There is an image segmentation functionality. In this document we use the term segmentation to mean subdividing an image, e.g. in our case a 2D image obtained from the forward-facing camera of an AR headset, into areas, with these areas for the most part identifying areas covered by objects of interest. (Other areas defined by the segmentation may indicate areas that are not of interest, such as background.) Further detail on segmentation can be found in:

Chapter 1 of the textbook Gonzalez and Woods "Digital Image Processing" 3rd edition (2008), pp. 3 to 18, ISBN 013168728 the full contents of which are incorporated herein by reference.

Segmentation may be based on thresholding, region growing and/or edge detection. Segmentation may involve the application of morphological operators. A morphological operator is understood to mean a mathematical operator used for shape analysis, and in particular for extracting image components that are useful in the representation and description of shape and in particular for determining the extent of objects in an image, e.g. by computing the boundary of an object. Example morphological operators are: dilation, erosion, opening, closing. Further detail can be found in:

Chapter 9, entitled "Morphological Image Processing", of the textbook Gonzalez and Woods ibid, pp. 627 to 688, ISBN 013168728, and the full contents of which are incorporated herein by reference.

Segmentation may be based on compositing multiple images, e.g. a conventional camera image and a thermal camera image of the same scene, or of multiple image frames of a video, or of two stills images of the same item taken at different times, e.g. before and after a task has been performed on or using the item, such as before and after a chemical process has been carried out in a microfluidic chip, or before and after a disassembly, cleaning and reassembly of a piece of manufacturing equipment.

Segmentation may be performed using any combination of standard image processing techniques, for example as described in the above-referenced textbook chapters. The images may be colour or grayscale. The segmentation to identify objects of interest in the image may involve any or all of the following image processing techniques:

1. Variance based analysis to identify the seed areas
2. Adaptive thresholding
3. Morphological operations
4. Contour identification
5. Contour merging based on proximity heuristic rules
6. Calculation of invariant image moments
7. Edge extraction (e.g. Sobel edge detection)
8. Curvature flow filtering
9. Superpixel clustering Segmentation can also be performed by neural networks with deep learning, which are being increasingly applied for this purpose. Convolutional neural networks (CNNs), for example, are becoming widely used. An example open source neural network is the VGG architecture from Oxford University available at: http://www.robots.ox.ac.uk/~vgg/research/very_deep/ which is described in Simonyan and Zisserman 2014 "Very Deep Convolutional Networks for Large-Scale Image Recognition." ArXiv Preprint ArXiv: 1409.1556. The VGG algorithm is available in versions VGG-M and VGG-16.

These image processing steps for performing segmentation are described by way of example and should not be interpreted as being in any way limitative.

There is an image pre-processing functionality which may include operators for deblurring, artefact removal, background removal, smoothing and so forth.

There is a compositing functionality for combining images. For example, this may include a warp transform component to align the images prior to combining.

There is an overlay generator for generating graphics overlays for the AR headsets, which may be coordinated with tracking of the scene viewed by the wearer of the headset so as to follow the operator moving within the cleanroom and moving his head and/or eyes.

There is a volume rendering functionality for generating 2D image renders from a 3D voxel map of a cleanroom as described above. With reference to the 3D cleanroom map and tracking of an operator's position within the cleanroom, it is possible without undue computational intensity to use a volume renderer to establish the view point (i.e. the 3D coordinates of the forward-facing camera on the AR headset) and view axis (i.e. the optical axis of the forward-facing camera) of the captured scene through analysis of the images being captured. Namely, the view point is already approximately known from the operator position tracking. An approximate view axis may also be known, e.g. by simultaneous image capture from one or more of the ceiling-mounted observation cameras or from gyro sensor input from the AR headset. Starting from an initial estimate of view point and perhaps also view axis, the values for these can be optimised by iterating computation of 2D image volume renderings from the 3D map in a way to maximize correlation between the iteratively computed (synthetic) rendered scene and the (real) captured scene. The volume rendering functionality can thus be used by the overlay generator to control changes in the overlay to update the overlay as the operator moves his/her head and moves within the cleanroom such that the overlay remains consistent with the scene that is visible by the operator.

There is a barcode reader functionality. The image capture for the barcode reader may be through a general-purpose forward-facing camera on the AR headset or a specialist handheld unit available to the operator. The barcode reader functionality may also be devolved to local processing on the AR headset.

There is an (M)BR interactive marking functionality to augment how MBR sections or BR sections are presented through an AR headset with highlighting. This image processing functionality is called by the control module in our system and effected by modifying the overlay image data transmitted to the AR headset so that the content items and/or associated fields in the MBR are rendered having regard to a criticality grading of the operator actions or other factor and in the BR (i.e. with populated fields) having regard to the acceptability or otherwise of the field entry values.

There is a graph interpreter functionality for interpreting spectrographic images. A graph can be analysed to extract peak information, such as peak position and peak integrals.

There is a segmentation-based image verifier which may use either or both of conventional segmentation and AI-based segmentation with a neural network. The segmentation-based image verifier is used to image process equipment images to determine whether the equipment is in a correct state in relation to the current stage of the manufacturing process.

FIGS. 9 and 10 show by way of example a section of an MBR used in the manufacture of a radiopharmaceutical in relation to preparation of the synthesis module and the HPLC (high performance liquid chromatography). FIGS. 9 and 10 may thus be considered as concrete examples of what is shown schematically in FIG. 6.

Subsections of the MBR are delivered to a display part of the AR glasses so that they can be read and completed by the operator.

The plain text content items of the MBR instructions can be augmented by a plurality of different visually perceptible markings, which may include for example:
  underlining (e.g. not-underline for normal and underline to convey a significance)
  bold (e.g. not-bold for normal and bold to convey a significance)
  font colour (e.g. black for normal and red, blue or green to convey respective significances)
  italic (e.g. not-italic for normal and italic to convey a significance)
  highlighting (e.g. with each of a plurality of colours having a different significance)

We refer to an MBR augmented with such markings as a highlighted MBR. This is implemented in our system by the control module of the computer application modifying the overlay image data transmitted to the AR headset so that the content items and/or associated fields are rendered having regard to a criticality grading of the operator actions or other factor(s).

In addition, some marking may be interactive during population of the MBR, i.e. during creation of a BR, with the state of completion of the BR and the flow through the BR being factors that may be taken account of to provide such interactive feedback to the operator. Examples of interactive features for a BR are:
  arrows (e.g. add arrows pointing to a field or text requiring attention)
  intermittent flashing or special colouring (e.g. to indicate an anomalous or missing entry which the current position in the process flow has passed over)
  speech bubbles emanating from a location in the MBR, e.g. a field or some text instructions, with text and/or drawing(s) providing information on a possible error or cause for concern
  a button or other user interface actuator to access a video clip emanating from a location in the MBR, e.g. a field or some text instructions.

We refer to a partly or wholly completed BR augmented with such interactive features as an interactively annotated BR.

FIGS. 11 and 12 show the same plain text as FIGS. 9 and 10, but with a highlighted MBR consisting of two marking modalities—grey-shading and bold—where:
  grey highlight (shading) is used to mark sensitive process steps;
  bold is used to mark steps that are one or more of: key importance, prone to failure inherently, or known root-cause of failure of past runs.

(Grey-shading and bold were merely used in this example to comply with patent drawing conventions—it will be appreciated that there are better ways to highlight subject matter, e.g. using colour.)

The operator can control the flow through the MBR steps (e.g. stop in the sense of pause, terminate, move back incrementally, move forward incrementally, continue to next step) through provision of appropriate user interface commands. The operator is also provided with appropriate user interface commands for populating the MBR fields with appropriate entries, whether these are merely check box fields requiring only an 'OK' or 'done' command input, or fields that require entry of a numeric value.

The user control is preferably done with a suitable hands-free user interface, such as using eye-, gesture- or voice-control. Alternatively, a hand-held clicker or numeric keypad or other device could be used.

The operator tasks include confirmation steps to tick a check box after completion of each associated task, whereupon the tick appears in the MBR, which the operator can also see through the AR display. Other operator tasks are associated with entering a value into an MBR field, which may be a measurement value such as a pressure. The value can be conveyed by voice control for example or by image capture with the headset forward-facing camera of an instrument display (e.g. a numeric display, or a dial-and-needle type display) and subsequent image processing to determine the displayed value in combination with a user input to confirm the determined value. The value then appears in the BR, which the operator can see through the AR display.

Communication between the AR headset and the computer system via a wireless communication channel ensures transfer of the operator's inputs into the BR.

The computer system may also additionally support the BR completion and other operator activity by delivering supplemental multimedia content from the training library to the operator via the AR headset, such as pictures, cartoons showing action sequences, 3D sketches, videos of a previous correct task completion and so forth. These may be used routinely, i.e. in all cases, to help an operator to fulfil a particularly critical or complex task in the workflow, or may only be provided on request of the operator, or if the computer system has reason to deduce that the operator is having difficulty with a task (e.g. is taking longer than usual to complete a task), or the computer system knows that the same user has had difficulty with a task in the recent past. The computer system may also make its decision to intervene with additional support based on the operator's experience and/or training level or general performance statistics for the operator.

Through use of a front-facing camera on the AR headset, it is possible to deliver images to the computer system which enable automated monitoring of the manufacturing process through image processing of the captured images (stills and video images). In this way it is possible to collect process parameters required for completion of the BR fields, whether they be process parameters that directly relate to an MBR field, such as a pressure value field, or process parameters needed to determine what should be entered in an MBR field, e.g. the slope of a graph or the baseline of a spectrum that is used to compute other parameters which are to be entered into an MBR field.

The following is an example list of parameters that may be critical to the manufacturing of a (radio)pharmaceutical using an automated synthesis-module:

1. All starting materials/excipients within expiry dates
2. All necessary auxiliary materials are placed properly in module
3. System pressure in range for individual process steps
4. Reactor-temperature in range
5. Flow valves correctly adjusted, e.g. as documented by numbers of turns from closed
6. Reactant import correct (i.e. precursor amount, radio-activity)
7. Product yield satisfactory Parameters of this kind can be monitored and transferred by the AR headset and processed by the computer application. Relevant parameters can be imported directly into the BR fields, i.e. those fields can be automatically populated by the computer system. This can be done as follows. Scene image data captured from the AR headset is sent to the computer apparatus running the computer application. The image data may for example be a stills image of a display of a piece of manufacturing equipment or analysis instrument used during the batch manufacture. The computer application then image processes the received scene image data to extract relevant data. This may simply be alphanumeric text data, e.g. sensor values such as for temperature or pressure, a sample/batch code number, an instrument ID. In other cases, the captured image may be of a graph or set of graphs on a computer monitor linked to or integrated with a piece of equipment, e.g. a spectrometer. The graphical data may include a graph and optionally also associated graph metadata. Graph metadata may include axis lines, axis labels and axis scale markings.

The extracted graphical and/or text data is then mapped to MBR fields with reference to the mapping data structure that provides links between the manufacturing process's operator actions and the MBR fields. The MBR fields can then be populated, assuming a suitable mapping is determined to exist. As feedback to the operator, the computer application then transmits overlay image data back to the connected AR headset to present to the operator with the results, i.e. to show the now-populated MBR fields to the operator, so the operator can check the entered values are correct or at least consistent with what the operator can see for himself from the relevant instrument or other equipment display.

The computer application may further refine this image capture and processing step by allowing the operator to select an MBR field, or linked group of MBR fields, at the same time as acquiring the image of the equipment. The selection of the MBR field by the operator may be done, for example, immediately before or after capturing the scene image data of the equipment display.

By selecting MBR fields, the computer application is told which fields it should attempt to map any extracted data to. That is, the computer application associates the selected field(s) with the received scene image data from the equipment display, so that the data extraction and mapping is restricted to the selected field(s). In this way it is possible to automatically populate an MBR field, or a linked group of MBR fields, through capture of equipment display images, e.g. a stills image. The operator can select that or those fields in the MBR through an AR headset GUI or other UI element interface. The equipment display image can then be captured responsive to the operator issuing an AR headset GUI command to capture a stills image (or video clip) when the display of the piece of equipment is in the scene. Alternatively, once the operator has selected the field(s) to be populated, the control module can capture video (or stills images in burst mode) and process those images to recognize the expected form of the instrument display (e.g. a particular kind of graph having expected features for the type of spectrograph to which the selected field(s) relate, or a particular number having a value consistent with a sensible range for a temperature that could be entered in a temperature value field).

Certain parameters may be evaluated for compliance with the MBR by numeric analysis, for example when the parameter is a single numerical value, e.g. a temperature or pressure, and a range of values of the parameter is permitted by the specification. The range may also be banded into two or more bands. For example, values lying within a most stringent confidence interval, i.e. a value lying in an ideal range, may be marked visually in the BR as such, or at least the operator's view of the BR, e.g. green font or green highlighting. Values not in the ideal range, but still falling within a second confidence interval which is within the range defined as OK in the specification, i.e. (just) acceptable values, can also be marked in some way, e.g. with amber highlighting. The difference between marking of ideal and acceptable can allow the operator and release party to pick up trends. Values outside the pre-set limits, i.e. unacceptable values, are labelled, e.g. with red font and/or pink highlighting, as a prompt to the operator or release party to take action. The visual cues on the parameters serve to help monitor the manufacturing process and pick up trends.

The control module of the computer apparatus may be configured to perform a quality control (QC), check of the batch based on an automated analysis of what has been entered in the fields of the BR. The QC check compares the field entries with what is permitted in those field entries according to a specification that forms part of the MBR. Possible outcomes from a QC check may include:
- the results indicate that the batch meets specification;
- the results indicate that the batch does not meet specification;
- the results indicate that the batch may not meet specification; and
- the results indicate a systematic error in the completion of the BR.

The last two outcome options may be omitted if desired.

For checking by a QP, the computer apparatus may transmit the BR and QC check outcome to a workstation for review. The QP can then make a batch release decision based on the information presented to him, including the QC check outcome from the system which will have the status of a recommendation. The batch release decision is then transmitted from the workstation to the computer apparatus and entered in a corresponding field of the BR.

As further material for the QP, scene image data recorded by the AR headset during the manufacture of the batch of pharmaceutical product, e.g. video footage recorded by a front-facing camera, may be provided. This further material will then be transmitted to the QP's workstation, perhaps in every case, but more likely on request of the QP.

The control module as part of the QP review may be further configured to permit establishment of a live audio communication channel between the QP workstation and the operator's AR headset to permit the QP to speak with the operator. Optionally also, the control module may permit establishment of a live video communication channel for transmitting live video feed from the AR headset to the QP workstation. The audio and video channels collectively enable the QP to view a live video feed from a forward-facing camera of the AR headset while speaking with the operator, e.g. to direct the operator to show him/her certain scenes. It is thus possible for the QP to ask the operator to view specific scenes of interest relevant to the batch release decision on behalf of the QP. The QP can then view the live video feed to assess the situation in the cleanroom. The extra review with the live video feed may be used for random spot checks or to assist the QP resolving an ambiguous or borderline result documented in the BR. The control module may be further configured to generate overlay image data relating to the QC check outcome and to transmit that overlay image data to the AR headset for view by the operator.

In a specific example, the above-mentioned four outcomes of such an automated quality control may be recommendations to the QP or operator as follows:

Batch determined safe to be released with no further action needed, i.e. the automated quality control check uncovered no reasons why the QP may not release the batch.

Batch not safe to release with no further action needed, i.e. the automated quality control check has uncovered data that should inevitably lead to a rejection decision, e.g. large quantities of an impurity at levels significantly above what is permitted have been identified.

Batch release cannot be recommended based on automated interpretation alone. The QP should make his or her own decision. Based on the automated check, the QP should pay attention to the following list of features determined by the automated interpretation to have possibly involved some subjectivity which could affect the release decision. (Here the ones that are relevant in each case based on the automated check will be listed as being potentially suspect, whereas any ones that the automated check had no concerns about may also be listed as such.)

Batch release not possible, since results cannot be interpreted with an automated check process. The results appear to have a systematic error, i.e. bear no resemblance to what is expected or have gaps. Check for systemic error, such as device malfunction or failure to load sample. Possibly carry out new test and resubmit results for analysis.

In each case, and in particular the second case, based on the outcome from the automated quality control check, the releasing party (i.e. QP) can thoroughly check sensitive release steps by reviewing the stored data relating to how the results were acquired and interpreted. In addition, the QP may request the operator provide live video feed from the instrument which provided the results with the sample loaded.

If the QP uncovers a clear error by the operator in respect of interpretation of the results, e.g. incorrect baseline positioning on a spectrograph, the computer application may also provide some post-processing functionality, e.g. the QP may be provided with GUI tools to re-position the baseline and the post-processing functionality may then recalculate the results. On approval by the QP, these interpretation changes and the associated results can then be entered into the corresponding BR fields instead of the originally entered values.

With this approach, centralised or distributed release becomes possible, since all parties are connected over a computer network and all relevant data is to hand, thereby allowing organisations to significantly reduce human resources and in particularly more efficiently use their expert QPs. A higher number of batch release decisions may be possible per day.

Figure 13:
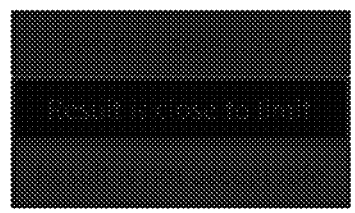
FIG. 13 shows an excerpt from example documentation as marked with quality control feedback.

FIG. 13 shows an excerpt from example documentation as marked with quality control feedback. The computer application for the AR-supported manufacturing process may have directly populated the BR data responsive to input via the AR headset. For quality control feedback to the operator, the field entries are marked with visual cues. The visual cues highlight whether the entry has an ideal value (pass), a value that is within specification but close to the limit (qualified pass), or an out of specification value (fail). Although not shown in view of non-use of colour, all the field entries can be displayed with a coloured font, e.g. blue, whereas all the static field labels in the first three columns are displayed with black font. In addition, the field entries, i.e. the numeric values in the "Test Result(s)" column and the pass/fail in the "Pass/Fail" column, are marked with coloured highlighting—green for ideal, amber for not ideal but nevertheless within specification, and pink for fail. The fail results and close-to-limit results are specifically marked with bubbles in view of the non-use of colour.

Standard quality control tests for pharmaceutical products include: chromatographic purity tests, mass-spectroscopy measurements and nuclear magnetic resonance (NMR) spectroscopy measurements. Such tests are characterised by compound specific patterns that are used for compound identification and purity checks.

The AR headset collects the necessary data (stills image capture through the forward-facing camera) directly from the monitor or other display of the measuring instrument, e.g. from the display of the instrument's control computer. The captured stills image is image processed, e.g. the chromatographic image including the chromatograph, or the NMR-image including a graph of the NMR spectrum. Through image processing, values for the parameters to be entered into the relevant fields of the BR are computed and then these fields are automatically populated with the computed values. In many cases, a BR field will be for entering the value of an individual parameter. However, in some cases one field may be for entering a whole table of parameter values, e.g. listing the species of each line in a chromatograph together with its wavelength position and integrated intensity. Pattern recognition algorithms (known to a person skilled in the art) are used to compare the imported chromatogram, NMR spectrum etc. to a pre-set standard trace.

The numeric parameter table is processed analogously. The imported values are used to calculate parameter values for parameters relating to, for example, (radio)chemical purity and compound integrity. The calculated parameter values are entered into the BR. The calculated parameter values are also compared to specification values and marked in the BR as to whether they are within an acceptable range and optionally also how closely they conform to ideal values within the acceptable range.

FIG. 14A shows a blank table that is a checklist of all the components and reagents as needed to carry out a particular set of operator actions associated with a manufacturing step as may form part of an MBR.

FIG. 14B is a populated version of FIG. 14A, i.e. the BR version. Conventionally, after having collected together all the components and reagents, the operator would enter the lot numbers of each, and also their expiry dates, into the relevant columns of the table. However, in the present system, as described further above, there is an integrated barcode reader functionality which may be based on AR headset image capture with its forward-facing camera and lookup in an inventory database. Not only does this allow automated population of the components and reagents table with lot numbers and expiry dates, but also quality control marking can be added. For example, as illustrated, the out-of-date product with an elapsed expiry data of 07/2019 has had its lot number and expiry date highlighted pink, whereas all other entries with in-date product have their lot numbers and expiry dates highlighted green. Moreover, missing items can also be highlighted or otherwise marked. This may be only done when the table is in a state of near completion with a small proportion of entries still missing. In this example, the "Neptis PSMA1007 disposable cassette" is missing, so the text entry labelling the item and the document where it is specified (content item) has been underlined and also highlighted yellow.

FIGS. 15A and 15B show an example list of pieces of equipment used during a batch manufacturing process as may form part of an MBR and corresponding BR respectively.

The example MBR extract illustrated requires use of an isolator, synthesizer, precision balance and a dose calibrator, and requires the instrument identifier for the individual instrument that is used to manufacture each batch to be recorded in the BR. The instrument identifier has in this example the format of an integer between 1 and 999. As can be seen in FIG. 15B, the entry is highlighted (e.g. pink) to give visual feedback to the operator through the overlay image that there is a syntax error in this entry, thereby prompting the operator to re-enter the instrument identifier.

While the above description envisaged operator support during a manufacturing process, the same approach can be used for operator training Operator training uses the above-mentioned training library where training materials are stored. In a training mode, all training units associated with a particular group of actions on which the operator is being trained may be mandated. The training mode may additionally make use of the above-mentioned operator scoring unit. For example, a test, dummy or mock campaign can be run without using precious ingredients. The training may cover a whole manufacturing process from start to finish of a particular pharmaceutical compound, or may be restricted to training on a particular part of the process, either specific to a compound, or specific to use of a particular diagnostic instrument or piece of production equipment. A new, untrained or partly trained operator is more intensively guided by the AR headset than would be the case in normal production for a fully trained operator. No physical trainer presence is necessary on site. The trainer can be off site and monitor the trainee operator either live or offline by watching either a live feed or stored content. In the case of a live feed, the trainer can watch the feed from the AR headset's forward-facing camera in combination with a live view of the BR as it is being completed. In the case of stored content, the trainer can access the same content at a later time. A trainer also has the option of watching a batch of trainees in parallel, by switching from one live feed to another, to replicate what an on-site trainer might do by wandering from person to person in the cleanroom to observe their activities. To verify the operations, successful or otherwise, a centralised or distributed training-evaluation is thus performed remotely by one or more trainer(s) by evaluating the received training video- and machine sequences continuously collected during the operation(s) and submitted automatically to the computer application by the AR headset. Based on the evaluation, personalised additional training plans can be generated for individual operators.

It will further be appreciated that the proposed system provides a fluid boundary between guidance during manufacturing and training By this we mean that the system lends itself to personalised support of individual operators. For example, an operator's past performance, either overall or per individual process step, can be used to tailor the AR-based support provided to the operator as he or she is manufacturing a batch. The operator can thus always be given personalised support, e.g. to avoid repeating previous errors or to help the operator speed up his or her performance of a particular process step if statistical analysis shows the operator has difficulty completing that step in a timely fashion. The personalised support should translate into better yields, quicker manufacturing and also reduce the need for remedial training outside the context of normal manufacturing.

Another feature of the computer-automated and AR-supported (M)BR management system is a graphical analysis interface for processing graphs as delivered by a spectroscopic or chromatographic measurement.

Figure 16:
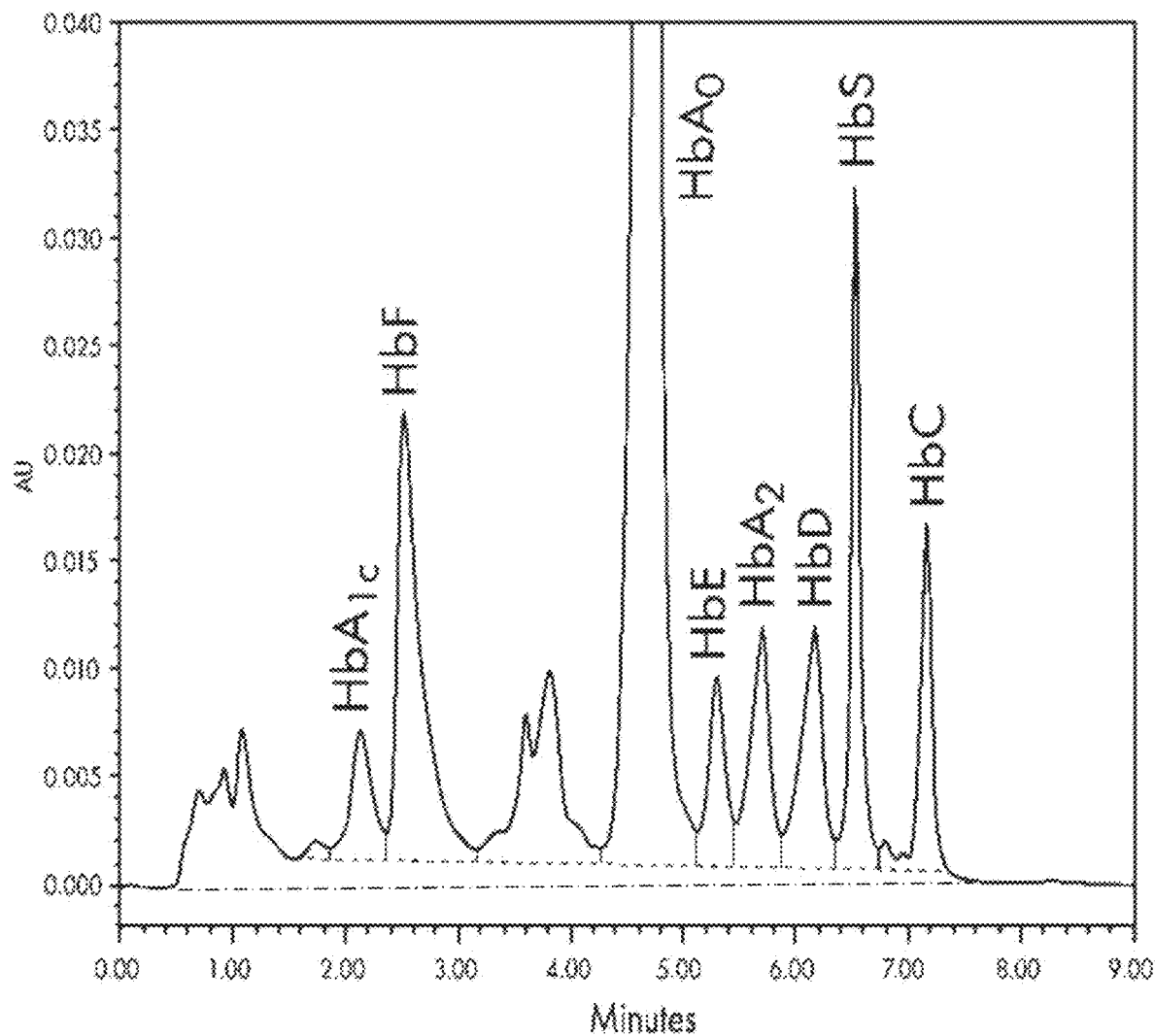
FIG. 16 is an example chromatogram.

FIG. 16 is an example chromatogram where the peaks correspond to different haemoglobin variants: HbA0 non-glycated haemoglobin; HbA2 normal variant haemoglobin; HbA1c glucose-bound haemoglobin etc. Two baselines are shown; a first with a dashed line and, slightly below that, another with a dot-dashed line. The y-axis is in arbitrary units (AU) reflecting the absorption of the compounds at a certain wavelength (e.g. in the ultra-violet (UV) range) or counts per unit time (e.g. gamma-, beta- or alpha-rays). The x-axis is in units of time (e.g. minutes as shown) based on the retention time of analytes on the solid-phase extraction material, in which the most hydrophilic compounds elute first followed by the less hydrophilic compounds in order of decreasing hydrophilicity when a so called reverse-phase material is used as the solid phase or vice versa with a "normal"-phase silica-based solid phase material. The relative abundance of each compound can be determined from the relative magnitudes of the integrals of each peak both for visible, UV or infra-red (IR) spectroscopic (light) signals and radiation signals in case of radiation detection. Thus, either method allows for a quantitative assessment of the chemical purity through light-signals or of the radiochemical purity through radioactive particle detection.

For quality control and batch release, the BR will typically include spectroscopic results in graph form, such as chromatograms as shown in FIG. 16. The MBR thus includes a group of fields that are to be populated with and from the results of a spectroscopy measurement and analysis. The mapping data structure of the computer application includes links between ones of the operator actions involved in obtaining and analysing the spectroscopic results and ones of the content items and associated fields that relate to the spectroscopic measurement and analysis. The spectroscopic measurement and analysis will typically be for quality control of a batch, e.g. to check a synthesis has been performed successfully, to measure impurity levels etc.

The process is performed as follows. After having established a data communication connection to the AR headset, a spectrograph image can be captured by the AR headset which shows results of the spectroscopic analysis. This will typically be displayed on a computer display of a computer in the cleanroom that is integrated with or connected to the spectroscopy instrument and is running specialist software application for image presentation and analysis of the spectroscopy image. The spectrograph image is thus received by the computer application as scene image data from the connected AR headset. The control module of the computer application is then configured to process the received scene image data with the aid of the graph interpreter functionality contained in the image processing unit 84 to extract a graph and associated graph metadata from the spectrograph image, wherein the graph includes a plurality of peaks. The control module then interprets the peaks of the graph with reference to the graph metadata to obtain peak data. The peak data may include position values (i.e. abscissae) for the peaks and integral values for the peaks.

From these processing steps, it is then possible for the computer application to populate the spectroscopic analysis fields with the graph, its associated graph metadata and the peak data. The population is done with reference to the mapping data structure. Feedback is given to the operator by transmitting overlay image data back to the connected AR headset to present to the operator the populated spectroscopic analysis fields for checking and approval/rejection. In response, the computer apparatus receives back user interface commands from the connected AR headset to accept or reject the populated spectroscopic analysis fields. There may be an option for the user to re-perform the spectrographic image capture using the same experimental results as before, i.e. not redoing the spectroscopy, rather only recapturing another image of the original results. This may be useful if, for example, the original image quality was perhaps not good and can be improved upon.

The AR headset may capture the necessary spectrograph image data by stills image capture from the graphical user interface of the spectroscopy instrument through the AR-headset's forward-facing camera. This may be from a monitor or other display of the measuring instrument, e.g. from the display of the instrument's control computer. If needed, a user is prompted to set or approve decisions that may be subjective of the kind discussed above, e.g. decisions that depend on a baseline being positioned, peak separation near the resolution limit, peak start and end values (e.g. in wavelength or time), peak labelling (e.g. there may be two or more molecules that are associated with the same or very similar peak wavelengths). The UI including GUI used for handling AR headset to processing computer apparatus communication when processing the spectrograph may be the AR-headset display in the case that the operator is responsible for this, or a separate GUI associated with a computer that has received the spectrograph, which could be under the control of the operator, or another member of staff, such as a spectroscopy expert, located remotely. Even if a separate computer monitor is used as the GUI for the interpretation, the person performing the interpretation can, and may be required to, wear an AR-headset so that the interpretation process is documented.

The values for the parameters to be entered into the relevant fields of the BR are then computed and then these MBR fields automatically populated with the computed values. In many cases, a BR field will be for entering the value of an individual parameter. However, in some cases one field may be for entering a whole table of parameter values, e.g. listing the species of each line in a chromatograph together with its wavelength position and integrated intensity, or to receive a graphics object, such as an image of the graph.

In certain kinds of spectrographic images, it is necessary to define a baseline to remove background signal and thereby ensure that the integral values are more accurate. The baseline thus acts as an ordinate zero line, which may be used when calculating peak integral values and perhaps also for calculating peak position values. The baseline may be straight or may be curved, e.g. to follow a line that could be determined from interpolation. The baseline has a significant effect on the calculated peak integral values and to a lesser extent will shift peak position values a little to the extent the baseline has a non-zero slope. However, placement of the baseline is often subjective and something as discussed above. The operator is given the opportunity to check and approve the baseline through the control module transmitting overlay image data to the operator's AR headset to present the graph with a baseline positioned thereon. The UI of the AR headset can use its regular user interface commands to accept or reject the baseline. The UI may also be provided with tools to allow the repositioning of the baseline. During any such repositioning, the baseline can be shown interactively to the operator by amending the overlay image data. The accepted baseline is then itself saved as part of the graph metadata, i.e. is applied to populate a spectroscopic analysis field for that purpose. The initial baseline position transmitted in the overlay image data may be one that has been determined automatically by the computer apparatus from the graph. Alternatively, the spectrograph image captured by the AR headset may already have a baseline on it, and the processing of the received scene image data may further extract the baseline as part of the graph metadata. This extracted baseline may then provide the initial baseline position transmitted in the overlay image data. Another alternative is to provide a UI tool for the AR headset which allows the operator to define an initial baseline position.

The control module is further configured to assign attribute labels to one or more of the peaks. The MBR may specify a list of attributes which should be assigned to peaks—providing such a peak is discernible in the spectrographic image. The attribute labels assigned to the peaks may, for example, be electronic transitions or vibrational modes, or molecular or atomic species. The attribute labels may be assigned to peaks by the computer apparatus in a number of ways or combinations thereof. The assignment may be done in an automated way by processing of the graph. The assignment may be via user interface commands issued by the operator and sent to the computer apparatus from the AR headset. The assignment may have already taken place in specialist analysis software built into the spectroscopic instrument (or its control computer) and thus may have already been displayed as text labels on the spectrograph image captured by the AR headset. In this case, the attribute label assignment can take place by the computer apparatus processing the spectrograph image to extract this information.

The labelled and integrated peaks enable relative abundance values to be determined between the attributes based on ratios of the peak integral values. The relative abundance value can then be used as an impurity level when ratioed against the integral value of a dominant peak attributed to a known non-impurity molecular or atomic species of a known absolute percentage abundance in the pharmaceutical product.

The computer apparatus may interpret the graph with reference to pre-existing and already interpreted graphs stored in a graph library. The pre-existing graphs for comparison may be selected based on being from the same kind of spectroscopic analysis using the same kind of spectroscopic instrument on a different batch of the same pharmaceutical product. The selection may be further restricted to only the same instrument. The interpretation can thus be benchmarked and assisted by comparison with one or more a priori known spectrographs of "good" batches (i.e. batches within specification) and/or other spectrographs of a priori known "bad" batches (e.g. batches with particular impurities present at levels that are out of specification).

By using the AR-tool the process of chromatogram acquisition and optionally also interpretation is:
  Recorded for later review by the QP at the time of deciding on batch release.
  Done while the QP is remotely present observing the process live.
  Supported by image processing comparing the spectrograph that has been acquired with benchmark spectrographs of good and/or bad batch spectrographs.

Video and other data which record the operator's actions in capturing and interpreting the spectrograph are captured in real-time by the AR-headset and are stored as an integral part of the BR documentation.

The image processing of the spectrograph, together with any input given to the image processing by the operator in selecting or setting parameter values, such as peak positions and baselines, thus allows an automated quality control check.

An automated analysis of what has been entered in the spectroscopic analysis fields of the BR can be used by the computer apparatus to perform a QC check. The QC check compares the spectroscopic analysis field entries with what is permitted in those field entries according to a specification that forms part of the MBR. Outcomes and further actions in relation to interaction with a QP can be as described further above in relation to a general QC check. The automated analysis of the spectrographic analysis fields may be done through comparison to results from a priori known good and/or bad spectrographs. If the spectrograph appears systematically flawed, the operator may be prompted to check for a systemic error on the instrument, such as device malfunction or failure to load sample. The operator may then possibly be permitted to carry out a new spectroscopic test and submit the new spectrograph for analysis. In case of a clear error by the operator in respect of interpretation of the spectrograph, e.g. incorrect baseline positioning, the computer application may provide the QP or operator with GUI tools to re-position the baseline. The graph can then be reanalysed, e.g. by recalculating peak integrals to then recompute relative abundances of impurities. On approval by the QP, these interpretation changes and the associated results can then be entered into the corresponding BR fields instead of the originally entered values.

An AR-supported process control function is provided to support batch-manufacturing and to make batch release recommendations, or even decisions. Control functions may relate to critical process steps such as the correct assembly of parts used in the manufacture and adherence to specified manufacturing parameters (e.g. pressure) at crucial times during a manufacturing process, e.g. before starting a synthesis.

The AR headset is intended to be the one worn by an operator responsible for having set up the equipment, i.e. the operator who has carried out a sequence of operator actions to set up the equipment as specified in the MBR and documented by the operator in the corresponding BR.

The AR-supported manufacturing process permits the integration of process decision points in the process flow which gate progression to a subsequent part of the process and also can be involved in gating release decisions on the finished manufactured product by a Qualified Person (QP) according to the four-eyes-principle.

The computer apparatus is configured to provide a process control function to check whether a piece of equipment has been set up correctly to carry out a manufacturing process step. After establishing a data communication connection to an AR headset worn by an operator, the computer apparatus receives scene image data from the connected AR headset of an image captured by the AR headset. The received scene image data is processed to identify an image of the piece of equipment and make a determination of its correct or incorrect set up. Based on the result the computer apparatus transmits data to the connected AR headset conveying an indication of correct or incorrect set up. The processing of the scene image data attempts to segment a pre-defined plurality of objects from the equipment image, wherein the processing makes its determination of correct or incorrect set up by checking each segmented object. The transmitted data may include overlay image data for the AR headset to augment the scene by providing an indication of at least incorrectly set up segmented objects and optionally also an indication of correctly set up objects. For example, a green-wash tick or a red-wash cross may be overlaid on the correctly and incorrectly set up objects. In addition, the transmitted data includes an indication of any of the pre-defined objects that the computer apparatus was unable to segment from the equipment image. For example, if four different vials are expected and only three have been segmented, then the transmitted data may inform the operator about the missing vial. This feedback content may include audio, non-augmented overlay image data such as a text descriptor, e.g. arranged as a banner at the bottom of the scene, or augmented overlay image data, e.g. highlighting the location in the equipment image where the vial should be present, but is absent.

The gating decisions are facilitated by tests enabled by input received via the operator's AR headset and carried out by a computer system integrated in the AR headset or, more likely, in operative communication with the AR headset. In particular, the tests may be based on image acquisition by the AR headset combined with image processing of the acquired images. In some cases, it may even be permitted to use the outcome of the image processing (in combination with an automated check of the BR) as a substitute for the QP making the batch release decision. A hybrid system may use the fully automated process as a first step, and, if the automated process decides the batch must be discarded, to rely on that decision without intervention by a QP, and then proceed to a second step of seeking approval from a QP only if the batch was approved by the automated process. The QP is thus saved the time of looking at undoubtedly defective batches, e.g. a radiopharmaceutical batch that lacked any significant radioactivity as measured by a radiation sensor, or any pharmaceutical batch determined in which there is insufficient liquid in the product vial, as for example determined with reference to a meniscus level determination made from an image of the product vial. The hybrid system thus in effect requires two approvals for batch release, first by the automated system and then by a QP. Alternatively, the first step may be viewed as providing the QP with advice and/or recommendations to support the QP coming to the correct decision about the batch quickly and reliably.

We now consider the example of operator assembly of a synthesis module, which involves the following process steps:

1. The operator fetches a synthesis module which includes a blank vial holder. The vial holder has a plurality of vial docking locations where specific reagent vials are to be docked.
2. The operator retrieves each reagent vial in turn from one or more boxes.
3. Each reagent vial has its barcode or individual id-number scanned for identification. The barcode scanning may be integrated in the AR headset using the forward-facing camera or done with a separate barcode reader. Based on the scan, the vial is identified. The expiry date/time may be checked by the computer system and the result displayed to the operator on the AR headset display, which the user can use as a prompt to check the corresponding check box in the BR.
4. The operator places the reagent vial into its designated docking location on the vial holder. This activity may be supported by the AR headset. For example, the forward-facing camera may capture video of the vial holder which is image processed to segment the image and identify the docking location for the reagent vial currently being held by the operator, e.g. as assumed by the most recently scanned vial or as tracked in the video after its scanning. The correct docking location can then be highlighted with a suitable overlay on the AR display, such as an arrow pointing to the docking station aperture or a highlight of the rim of the docking station. The image processing will typically not be carried out in the AR headset, but rather at a processing node which may be located at the manufacturing site, or further afield, such as at the central site.
5. After all vials have been docked and/or all docking locations filled with vials, a separate check may be performed supported by the AR headset as follows. (Alternatively, this could be instead of the previous step.) An image of the assembled holder is acquired by the forward-facing camera optionally with all the vials' barcodes being visible and readable from the image. Image processing is then carried out on the image using pattern recognition and/or artificial intelligence (AI) algorithms. For example, a warp transform could be performed between one or more ground truth images and the acquired image to determine whether there is a match, the image processing being optionally augmented by the barcode scan results from the same image to verify the correct reagents are in the intended docking locations. The image processing may also be used to verify other aspects of the integrity of the assembly of the synthesis module, for example that each tube is correctly in place both in terms of its routing and an appropriate connection at each end. A copy of the image is appended to the BR. In terms of the AR-support, if the checking procedure is to verify correct placement of say 6 vials and correct connection of say three tubes (each with routing and 2 end connections to be verified), then there are 15 individual checks. The AR display can be provided with an overlay of green ticks for a 'pass' (or red crosses for a 'fail') for each of the checks, i.e. 15 here. This gives the operator the opportunity of correcting any errors, to the extent the MBR allows correction, and if not may recommend the operator to discard the module, e.g. by interactively annotating the BR so that the text stating, for example, "discard module" is flashed. Visual confirmation of the results of the image processing checks may be supplemented or replaced by audio, e.g. speech, feedback to the operator via the AR headset's headphones. An additional control may be to check fill levels or fill amounts of the vials if the acquired images are of sufficient quality. Fill level control may be assisted by the vials having fill level markers which can be imaged and used by the image processing.

Procedures of this kind can be performed for any critical synthesis (i.e. reaction) preparation steps and subsequent synthesis performing steps.

One kind of equipment set up involves arranging vials in set locations in relation to the equipment, e.g. in receiving locations sometimes referred to as docking stations. As a check that the vials are correctly arranged and are all present, an image can be captured with the AR headset and sent to the computer apparatus for processing.

The computer application running on the computer apparatus then processes the received scene image data to identify any vials found in the scene and to identify whether they are at their set locations. A determination of correct or incorrect equipment set up can then follow. The manufacturing process step related to the equipment set-up may be a chemical synthesis step, a purification step, a physical step such as tablet formation in a press, packaging in a blister pack or a liquid handling step such as vial preparation or well plate filling, an pharmaceutical product analysis step, such as with a spectrometer.

The computer application can send back feedback information to the operator via the AR headset, e.g. as overlay image data (augmenting and/or non-augmenting), which provides an indication of the target docking station in case of an undocked vial and an indication of (in)correctness of the docking station in case of a docked vial. Missing vials may also be indicated in case there is an empty docking station and no compatible vial was recognised from the image.

Identification of vials or other items in the scene may make use of a machine-readable code reading function (barcode). Namely, the received scene image data can be processed to perform vial or other item identification on any vials or other items found in the scene image data by reading a machine-readable code attached to any such vial. In response to item identification through a barcode, data can be transmitted back to the AR headset to providing feedback information extracted through each code. For example, this may be in overlay image data presented to augment the scene being viewed by the operator.

The scene image data may be captured by a forward-facing camera that is integrated in the AR headset to capture images of scenes as viewed by the operator wearing the AR headset. The data may be transmitted as overlay image data, either augmenting the scene or as image data that does not augment the scene. The feedback information may provide an efficacy indication for the vial, a use-by-date, vial contents information, vial fill state. The feedback information may be in the form of text, audio or overlay image data, for example. The code may trigger lookup in an inventory database containing a record of an item linked to the code it was labelled with, and this lookup provides at least a part of the feedback information.

After completion of assembly, i.e. completion of the group of the operator actions relating to assembly of the synthesis module, a quality control check can be made to confirm (or deny) successful completion of the assembly. This can be implemented by the AR headset. Capturing an image, or perhaps multiple images from different directions, of the assembled module with its forward-facing camera. The image data is sent to the computer apparatus. The image data received from the AR headset is then processed to perform a holistic verification of correct synthesis module assembly, i.e. a binary result of correct/incorrect. The result is conveyed to the operator by transmitting data to the AR headset. The transmitted data may be in the form of overlay image data, in particular to augment the scene. Moreover, the overlay image data may provide a visual indication of correct/incorrect assembly of individual components and/or of the synthesis module as a whole.

Figure 17:
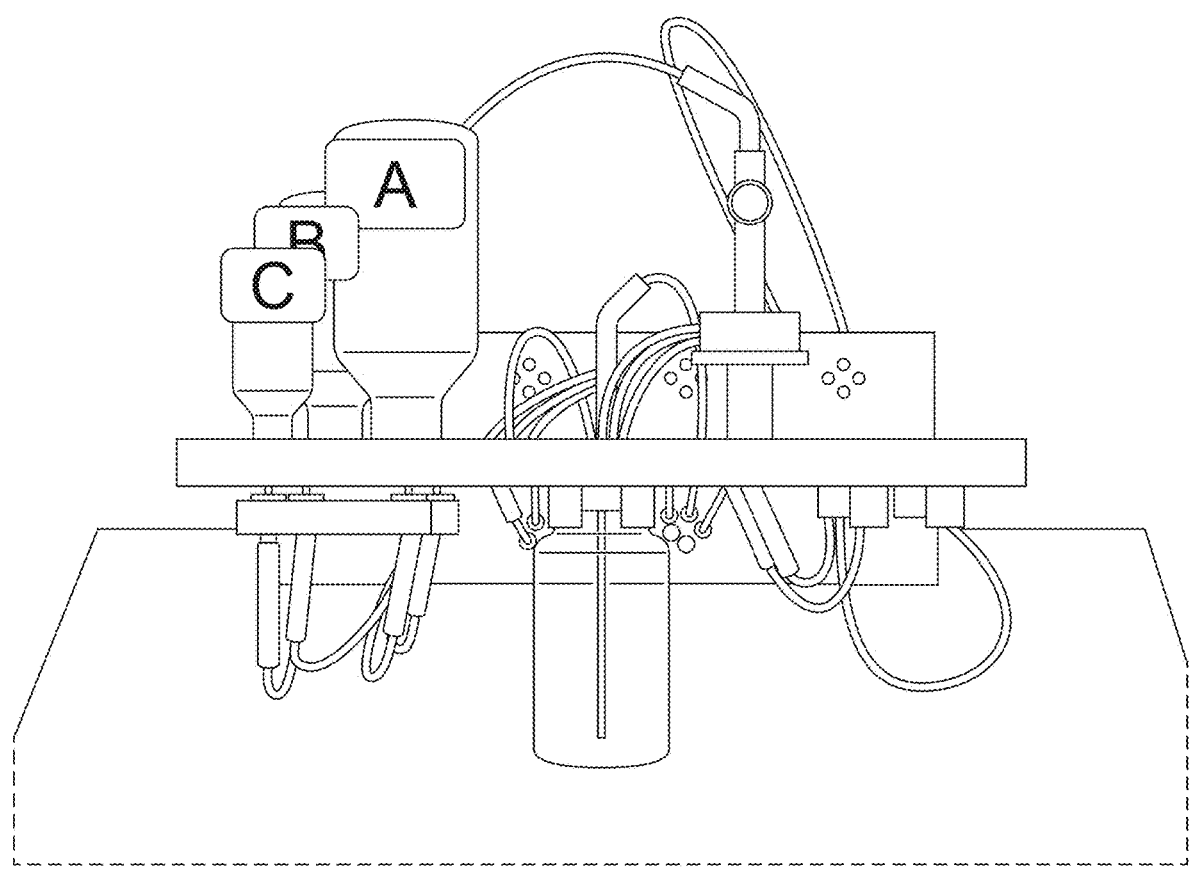
FIG. 17 shows an assembled synthesis module in which reagent vials have been arranged in docking stations of a substrate.

FIG. 17 shows by way of example an assembled synthesis module in which a variable number of reagent vials (e.g. four) are arranged in associated docking locations on a substrate-holder. To support the module assembly, the computer application in its process data structure includes a definition of a group of the operator actions relating to assembly of the synthesis module, e.g. in this case which will include actions of attaching a plurality of vials to specific ones of respective docking stations on the synthesis module. In addition, some actions may relate to making tube interconnections between vials and other parts of the module.

The illustrated synthesis module includes an assortment of tubes which connect the vials to a reaction-vial arranged below the main substrate. The vial-holder including the reaction-vial is connected to a purification device in a standard setup. Such purification devices can be solid-phase extraction (SPE) cartridge(s) or a liquid chromatography system (including but not limited to High Pressure Liquid Chromatography), and a Drug Substance (DS)/Drug Product (DP) batch-container. Such DS/DP batch-containers are can be connected to an automated or manual dispensing system. The labels A, B, C shown in FIG. 17 are schematic representations of labels derived from barcode reading of these vials as described above as presented to the operator via an overlay image transmitted to the AR headset.

The AR-supported assembly process is thus linked to the MBR processes both step-by-step through guidance of the assembly, as described further above, and additionally by way of an independent final check of the assembled item which does not rely on any of the intermediate guidance.

The final check may be gated on the four-eyes principle, i.e. may require sign off by a supervisor prior to carrying out the synthesis. In this case, the supervisor also has access to the results of the image processing checks. Alternatively, the automated checking by the image processing may serve as a substitute for the supervisor sign-off, if desired.

After synthesis another, similar image processing check may be carried out. This time in addition to the previous checks (some of which may be omitted at this stage) some new checks may be carried out, e.g. to check fill levels of the various vials to take account of the liquid transfer that should have taken place in the course of the synthesis. This post-synthesis image acquisition and processing procedure should of course be integrated in the batch release decision.

Another example is to build in a check that a safety plug, cap, drain or other item has been removed from the equipment. This may be any item that is provided to protect the equipment, or a consumable module that is fitted to the equipment, until use, but that is required to be removed prior to use. This may be the case when a sealed consumable item is loaded into the equipment as part of the set up, and a safety plug is required to be removed to unseal the consumable item and complete the set up. A cap may also be provided to prevent leaking of a tablet coating suspension onto tablets when coating is not being performed. The equipment image can then be segmented to identify whether the safety plug has been removed or is still present. The result can then be fed back to the operator by transmitting data back to the AR headset providing an indication of a need for safety plug removal. This transmitted data may include overlay image data for the AR headset which augments the operator's scene by providing an indication of a safety plug that is still in place. The object to be segmented may be the safety plug itself or may be a feature that is obscured when the safety plug is in place, but visible after it has been removed. The test of safety plug removal may be absence or presence of the safety plug in the equipment image, or presence of the safety plug in an expected position in the equipment image associated with it being in place (or removed).

Figure 18:
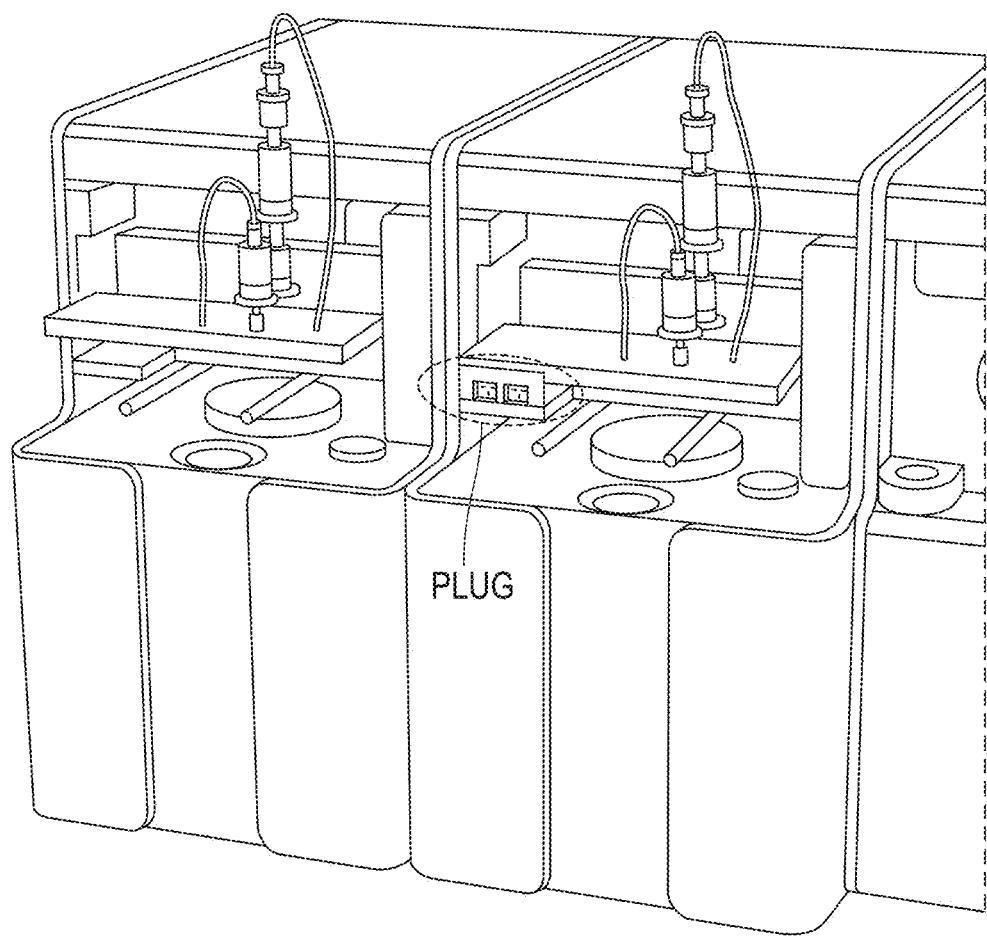
FIG. 18 shows images of two similar pieces of equipment, the right-hand image having a safety plug fitted and the left-hand image having it removed.

FIG. 18 shows two images alongside each other. The left image shows the equipment with the safety plug removed, whereas the right image shows the equipment with the safety plug in place.

Another example is to check the set up of a spraying apparatus that is used in tablet manufacture. A sprayer may be used in tablet manufacture for example for tablet coating, wurster coating, blending, granulating, bead coating or aseptic cleaning of vessels. The operator acquires a scene image from the forward-facing camera of the AR headset while the sprayer is spraying from its spray nozzle(s) in order to capture an image of the spray emission. A test spray may be performed for this purpose. The scene image data is sent to the computer apparatus for processing. The spray shape can be specified to be conical within a range of solid angles. The processing identifies whether the spray pattern is consistent with a correctly set up nozzle as specified. A blockage or partial blockage would be identified through asymmetry of the spray cone. An incorrect adjustment of the spray nozzle would be identified by a conical spray that lies outside the specified angular range.

It will be clear to one skilled in the art that many improvements and modifications can be made to the foregoing exemplary embodiments without departing from the scope of the present disclosure.

Figure 19:
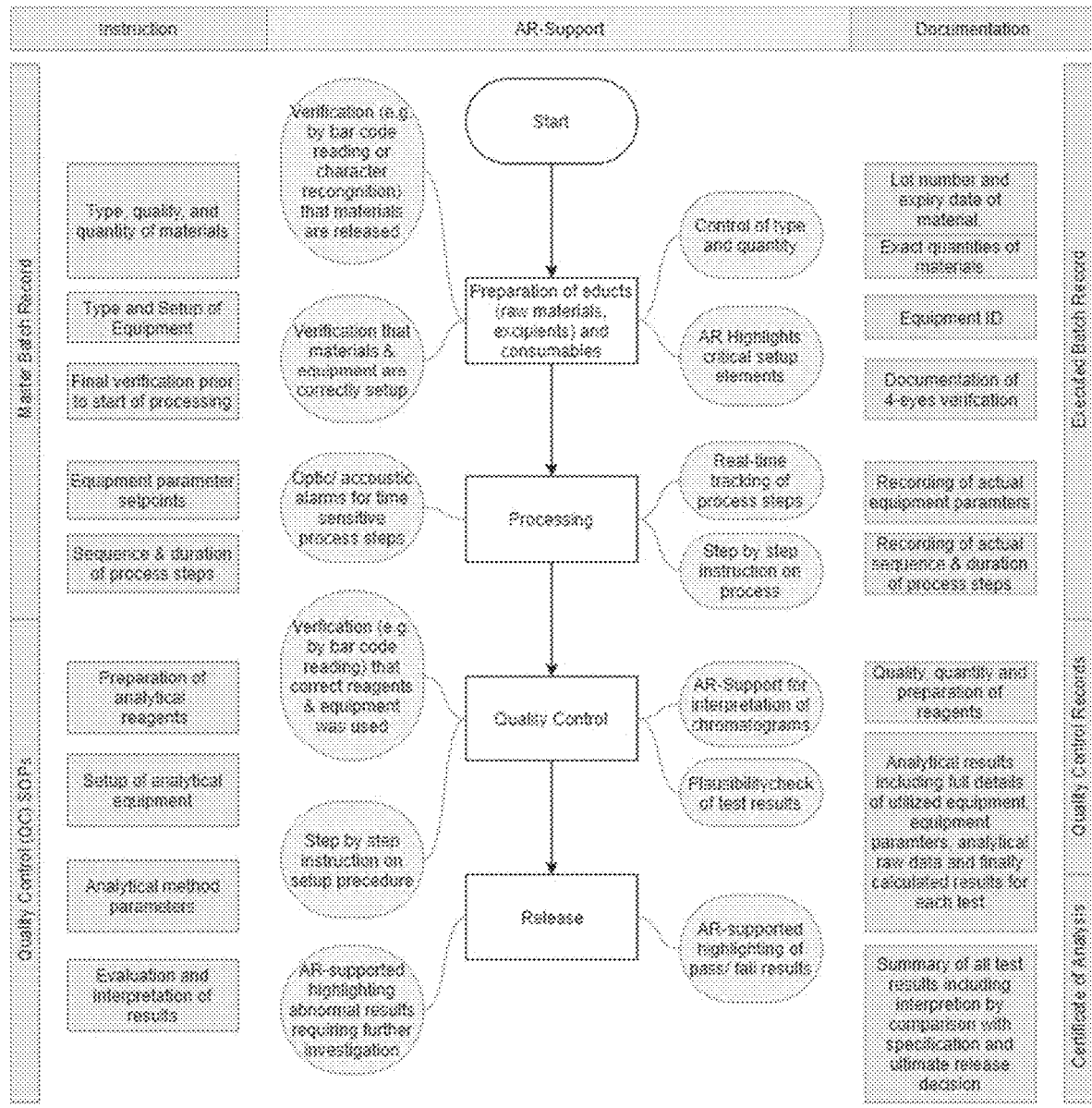
FIG. 19 is a conceptual summary chart showing features of the proposed AR-supported manufacturing processes and their interrelationships.

FIG. 19 is a conceptual summary chart showing features of the proposed AR-supported manufacturing processes and their interrelationships. The main stages in the pharmaceutical manufacturing process are shown in the spine of the drawing as a linear process flow, namely from start through preparation of educts and consumables, to the chemical processing steps of producing the compound or other pharmaceutical product, to the quality control, and finally to the release. AR support is provided at each stage as indicated in the rounded text boxes either side of the central spine. The associated instructions for the operators and QPs as specified in the MBR are shown in the left-hand column in the square text boxes. The documentation, i.e. compilation of the BR from the MBR is shown by the text boxes in the right-hand column. The content of the various text boxes is intended to provide a comprehensive overview, but is not an exhaustive listing of the features, rather a listing intended to provide a general understanding of the proposed approach.

For cleaning a pharmaceutical production line, documentation analogous to the MBR/BR combination is used. Namely, there is a line clearance protocol which specifies operator actions for cleaning the line, which are documented by the operator confirming each cleansing operator action has been performed and if relevant entering additional information, such as barcodes of cleaning product bottles, or any measurements or stills images taken at various points in the cleaning process. For example, FIGS. 6A & 6B and their description relating to the MBR and BR can be transferred over to, and taken as equivalent disclosures of, the line clearance protocol and a QC record. The operator's role in the line clearance process is primarily one of performing cleaning actions. Moreover, the QP role in the MBR/BR-driven manufacturing process is taken by the supervisor in the line clearance. (In the art of line clearance, the supervisor is sometimes referred to as a second person with reference to the fact that the operator should not be responsible for certifying his/her own cleaning actions.) Statements in the description of the manufacturing process further above relating to the QP can therefore be transferred over to, and taken as equivalent disclosures of the supervisor for line clearance.

Referring to FIG. 4, the operator responsible for the line clearance actions may have the tasks of cleaning any or all of the various cleanroom surfaces 44, 46, 48, the doors 7, fittings such as the observation cameras 34, table surfaces 42, other furniture surfaces, fixtures and fittings such as door handles, light fittings, windows, and external surfaces of pieces of equipment, such as instrument housings. In addition, other cleaning tasks will relate to cleaning specific pieces of equipment, such as a tablet press. The equipment cleaning may involve operator actions for dis-assembly and re-assembly as well as cleaning of individual equipment parts or surfaces and exchange of single-use or other consumable items, such as sterile plastics items or filters.

For cleaning of specific pieces of equipment, a stills image may be acquired after completion of cleaning by the forward-facing camera. Optionally, for comparison purposes, another stills image may be acquired before cleaning is commenced.

Image processing is then carried out on the stills image using conventional image processing as described above, e.g. with segmentation, and/or artificial intelligence algorithms using neural networks. For example, a warp transform could be performed between one or more ground truth images of examples of the piece of equipment known to have been clean (and/or other ground truth images of examples of the piece of equipment known to have been dirty) and the acquired image to determine whether there is a match. The result may identify areas that potentially need re-cleaning, which can be identified to the operator through appropriate overlay marking on the AR display, e.g. with an arrow to or circle around an area that is suspect.

The image processing may also be used to verify other aspects of the integrity of the cleansed item, e.g. if cleaning involves some dis-assembly and re-assembly then the image processing can be used to check that the reassembly was done correctly—again by comparison with ground truth images of the piece of equipment in a correctly assembled condition. If the item is determined to be incorrectly assembled, then an appropriate instruction can be delivered to the operator via the AR headset, e.g. as a voice message or as a display overlay. The display overlay may provide more specific diagnostic information about which part of the item is not correctly assembled.

Compared with the standard approach of checking boxes in the cleaning record, the AR-supported process using image capture from the forward-facing camera in combination with suitable image processing for both quality control and data acquisition, in combination optionally also with guidance through overlays on the AR display, reduces the risk of an operator missing a cleaning task to almost zero. External quality control from a supervisor is also more efficient, both in the sense of being a more efficient use of the supervisor's time and also since the supervisor can base clearance on stored and live stills and/or video images. The cleaning process can be better documented through acquisition of stills images and video footage, e.g. one or more video clips, as the cleaning is being carried out through the AR headset being worn by the operator carrying out the cleansing actions. Such information can make a significant contribution to the supervisor's verification by allowing the supervisor to gain confidence that the cleaning was done according to established procedures and with sufficient thoroughness.

The AR support obviates the need for a supervisor to enter the cleanroom or other restricted area (e.g. class A, B or C) to perform verification and therefore avoids the need for another person to spend time gowning up and avoids the inevitable contamination associated with an additional person spending time in the cleanroom. Gowning up takes some time due to the elaborate nature of the procedure. In addition, if supervisor verification is needed during a night shift, or other time when there are reduced staff levels on site, there may be a wait time until a suitably qualified staff member is available. The supervisor does not even need to be present at the same site, but could be anywhere in the world, so centralised or geographically distributed verification is enabled. Regarding improved quality, the supervisor can verify the line clearance based on a combination of logged video, stills footage and inspection of the electronic BR (or equivalent electronic document for cleaning protocols) and live viewing of the video feed from the AR headset being worn by the operator in combination with a two-way audio link between the supervisor and the operator via which they can talk to each other, e.g. for the supervisor to request that the operator shows him or her a certain part more closely through the live video feed. Overall, the AR-supported line clearance process enables simultaneously higher throughput and improved quality.

In the AR-supported process, the operator can call upon qualified staff located remotely outside the cleanroom and possibly at a remote site, such as a central facility. The remotely located supervisor reviews the recorded photographic stills images and video footage. The supervisor can also connect to watch live video through the operator's AR headset, for example for the operator to show particular areas more closely. After confirmation of cleanliness, the supervisor verification is documented in the electronic, i.e. paperless, cleaning documentation and/or BR for the batch about to be manufactured in a GMP/cGMP compliant manner Example A: Cleaning of a 24-Punch Rotor Tablet Press The operator disassembles the equipment (e.g. feeder upper punch, lower punch and dies) and then cleans the rotor. A specific procedure has to be followed for cleaning each of the 24 openings in which the dies are inserted.

The AR support and checking are configured to guide the operator through the process by tracking which openings have been subject to cleaning activity as the cleaning progresses, effectively marking off each opening as cleansed after it has been cleansed. This is done by capturing video images through the forward-facing camera and using image processing to identify when an opening is subject to cleaning activity by the operator. The cleaning process can also be supported by overlaying an arrow (or other marker) onto the AR display to point to the next opening that should be cleansed according to some logical sequence for cleaning the openings.

For quality control, the video footage of the cleaning process is stored for later review.

After cleaning of the openings is finished, a supervisor verifies the cleanliness by reviewing the video footage and the cleaning protocol document (analogous to a BR for manufacturing). In addition, the supervisor can inspect the condition of the punch rotor tablet press from a remote location by connecting to a live video feed through the forward-facing camera of the operator's AR headset while the operator is presenting the press for inspection.

Example B: Line Clearance in a Radiopharmaceutical Production Setting

The operator prepares the production suite for manufacturing of a new radiopharmaceutical product. The operator has to ensure that in particular the synthesis and dispensing hot cell do not contain any leftovers from the previous production batch. Since radiopharmaceutical products are usually parenteral, e.g. administered by injection, not orally, preparation has to be done under consideration of aseptic techniques to prevent contamination of cleanrooms with bacteria or other particles. At the same time, the operator has to consider radioactivity protection aspects. Last not least, the whole manufacturing operation, including any intermediate cleaning steps, has to be done under extreme time constraints, since the radiopharmaceutical product will contain an isotope with a short half-life, and hence have a short shelf-life.

After proper gowning, the operator enters the Class C (ISO 7) environment through personnel locks. The operator cleanses the synthesis hot cell by opening it after confirmation that radioactivity has decayed to safe levels. The operator removes all parts from the previous production and then acquires an image using the forward-facing camera to document the final status. Thereafter, the operator cleanses the dispensing hot cell (Class A, ISO 5). Since this isolator has to remain closed in order to maintain a high cleanliness status, the operator has to cleanse the dispensing hot cell using manipulators while viewing the cell through small lead glass windows. The forward-facing camera records video footage of this activity to provide proof that the operator has dealt with all the materials used in the previous manufacturing process.

Figure 20:
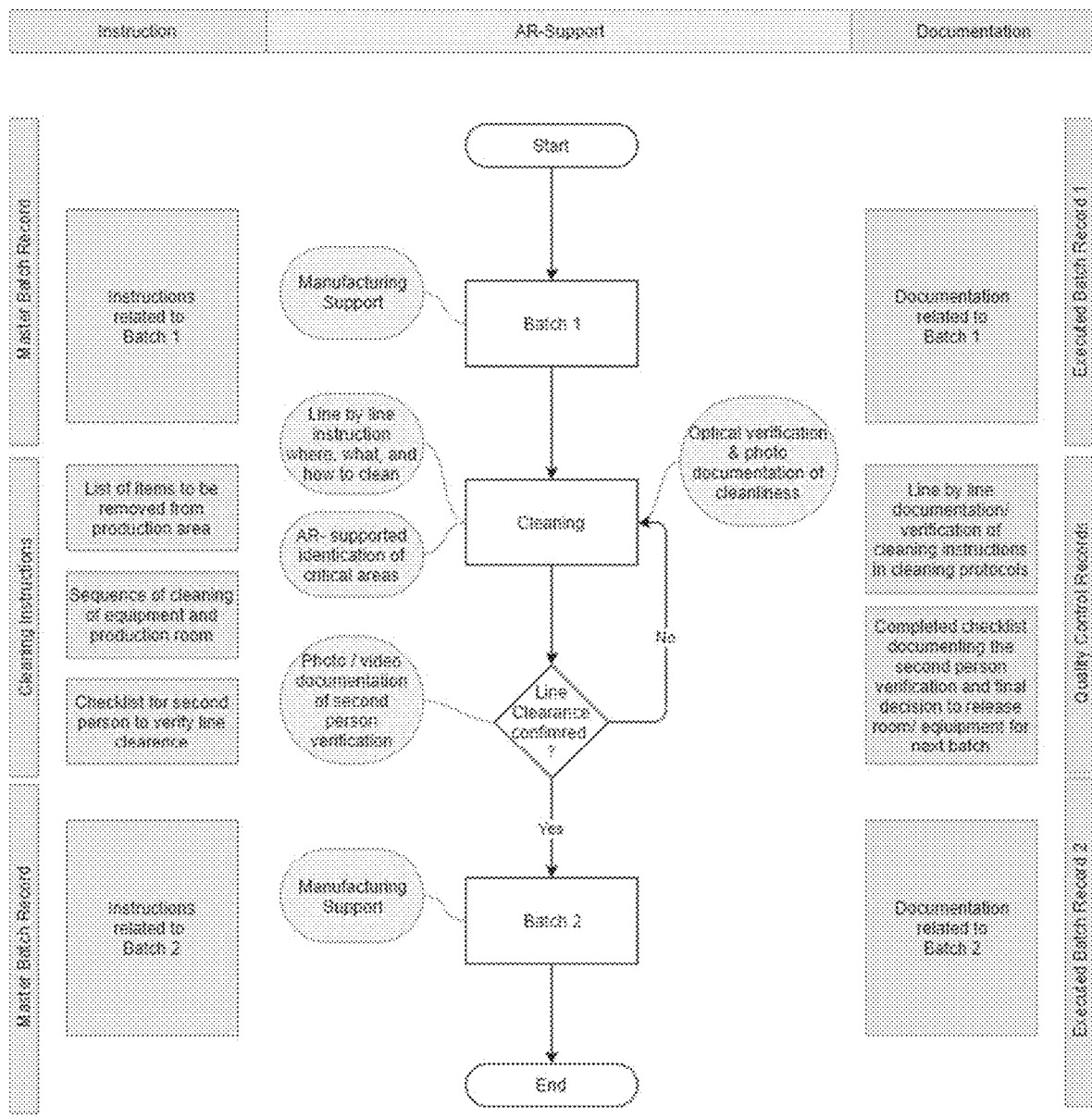
FIG. 20 is a conceptual summary chart showing features of the proposed AR-supported line clearance processes and their interrelationships.

FIG. 20 is a conceptual summary chart showing features of the proposed AR-supported line clearance process and their interrelationships. The main stages of the process are shown in the spine of the drawing as a linear process flow, namely from start through manufacture of a first batch of pharmaceutical product, to the cleaning process, to the clearance of the cleaning process, and to manufacture of a second batch of pharmaceutical product. AR support is provided at each stage as indicated in the rounded text boxes either side of the central spine. The associated instructions for the operators and for the verifying supervisors are shown in the left-hand column in the square text boxes. The MBR governs batch production procedures, whereas cleaning instructions govern the cleaning procedures. The documentation, i.e. compilation of the BR from the MBR, and the cleaning quality control record from the cleaning instructions, is shown by the text boxes in the right-hand column. The content of the various text boxes is intended to provide a comprehensive overview, but is not an exhaustive listing of the features, rather a listing intended to provide a general understanding of the proposed approach.

Further features and aspects of the disclosure are presented in the following numbered clauses.

A1. A computer apparatus configured to generate a batch record, BR, during manufacture of a batch of pharmaceutical product by populating a master batch record, MBR, the computer apparatus comprising:
  a process data structure defining a sequence of manufacturing process steps that are required to be carried out to manufacture a batch, the manufacturing process steps involving respective operator actions;
  an MBR comprising a plurality of content items and associated fields, wherein the fields are to be populated as an operator progresses through the operator actions;
  a mapping data structure that links operator actions to content items and associated fields; and
  a control module configured to:
    establish a data communication connection to an augmented reality, AR, headset worn by an operator responsible for manufacturing the batch;
    transmit overlay image data to the connected AR headset, the overlay image data presenting ones of the content items and associated fields to the operator in a way that follows the operator's progression through the operator actions as determined with reference to the mapping data structure and that is responsive to the operator populating the MBR fields;

receive user interface commands from the connected AR headset; and populate fields of the MBR, as presented to the operator in the overlay image data, responsive to receipt of the user interface commands A2. The computer apparatus of clause A1, wherein the control module is further configured to modify the overlay image data so that the content items and/or associated fields are rendered having regard to a criticality grading of the operator actions.

A3. The computer apparatus of clause A2, wherein the control module is further configured to store a plurality of operator profiles relating to at least one of: operator skill and operator track-record of individual persons, and wherein the criticality grading takes account of an operator profile selected for the operator carrying out the operator actions.

A4. The computer apparatus of clause A2 or 3, wherein the content items include text content and the overlay image data is modified by adding visually perceptible markings to distinguish between different portions of the text content having regard to said criticality grading.

A5. The computer apparatus of clause A1, further comprising a library of training units comprising one or more of video clips, stills images, text and audio, each training unit being associated with a specific operator action, group of operator actions or manufacturing process step, wherein the mapping data structure further provides links between ones of the operator actions and ones of the training units.

A6. The computer apparatus of clause A1, wherein the process data structure includes a definition of a group of the operator actions that relate to assembly of a synthesis module by attaching a plurality of vials to specific ones of respective docking stations on the synthesis module.

A7. The computer apparatus of clause A6, wherein the control module is further configured to:

receive scene image data from the connected AR headset of at least one image captured by the AR headset;

process the received scene image data to perform vial identification on any vials found in the scene image data by reading a machine-readable code attached to any such vial; and in response thereto transmit data to the connected AR headset providing feedback information extracted through each code.

A8. The computer apparatus of clause A6 or A7, wherein the control module is further configured to:

receive scene image data from the connected AR headset of at least one image captured by the AR headset;

process the received scene image data to identify any vials found in the scene and to identify any docking stations in the scene, at least ones that relate to identified vials, and in response thereto;

transmit data to the connected AR headset conveying at least one of:

an indication of docking station in case of an undocked vial; and an indication of correctness of docking station in case of a docked vial.

A9. The computer apparatus of clause A6, A7 or A8, wherein on completion of the group of the operator actions relating to assembly of the synthesis module the control module is further configured to:

receive scene image data from the connected AR headset of at least one image captured by the AR headset;

process the received scene image data to perform a holistic verification of correct synthesis module assembly; and responsive thereto transmit data to the connected AR headset conveying an indication of correctness of the assembly.

A10. The computer apparatus of clause A1, wherein the control module is further configured to:

receive scene image data from the connected AR headset of at least one image captured by the AR headset, wherein the at least one image is of a display of a piece of equipment used during the manufacture of the batch of pharmaceutical product;

process the received scene image data to extract at least one of: graphical data, including a graph and associated graph metadata; and text data;

map the extracted graphical and/or text data to at least one field of the MBR with reference to the mapping data structure;

populate the at least one field according to the mapping; and transmit overlay image data to the connected AR headset to present to the operator the at least one field as populated according to the extracted graphical and/or text data.

A11. The computer apparatus of clause 10, wherein the control module is further configured to:

receive a user interface command to select at least one field of the MBR from the connected AR headset;

associate the at least one selected field with the received scene image data from the equipment display; and apply the data extraction and mapping to the at least one selected field.

A12. The computer apparatus of clause A1, wherein the control module is further configured to:

perform a quality control, QC, check of the batch based on an automated analysis of what has been entered in the fields of the BR, wherein the quality control check compares the field entries with what is permitted in those field entries according to a specification that forms part of the MBR; and output a QC check outcome selected from the following:

the results indicate that the batch meets specification; and the results indicate that the batch does not meet specification; and optionally also:

the results indicate that the batch may not meet specification; and/or the results indicate a systematic error in the completion of the BR.

A13. The computer apparatus of a clause A12, wherein the control module is further configured to:

transmit the BR and QC check outcome to a workstation for review by a qualified person, QP;

receive a batch release decision from the workstation and enter it in a corresponding field of the BR.

A14. The computer apparatus of clause A13, wherein the control module is further configured to:

record at least a subset of scene image data received from the connected AR headset during the manufacture of the batch of pharmaceutical product, said recorded scene image data including video footage; and transmit at least some of the recorded scene image data to the workstation for review by the QP.

A15. The computer apparatus of clause 13 or 14, wherein the control module is further configured to:

establish a live audio communication channel between the QP's workstation and the operator's AR headset to permit the QP to speak with the operator; and establish a live video communication channel for transmitting live video feed from the AR headset to the QP workstation, thus enabling the QP to view a live video feed from the AR headset while being able to speak with the operator.

A16. A computer-implemented process for generating a batch record, BR, by populating a master batch record, MBR, as part of manufacture of a batch of pharmaceutical product by an operator wearing an augmented reality, AR, headset, the process comprising:
  providing a process data structure defining a sequence of manufacturing process steps required to be carried out to manufacture a batch, the batch manufacturing process steps involving respective operator actions;
  establishing a data communication connection between the AR headset and a computer apparatus configured to control the generation of the BR during manufacture;
  providing the computer apparatus with an MBR comprising a plurality of content items and associated fields, wherein the fields are to be populated as an operator progresses through the operator actions;
  providing the computer apparatus with a mapping data structure that links operator actions to content items and associated fields;
  transmitting overlay image data from the computer apparatus to the connected AR headset, the overlay image data presenting ones of the content items and associated fields to the operator in a way that follows the operator's progression through the operator actions as determined with reference to the mapping data structure and that is responsive to the operator populating the MBR fields; and
  generating the BR by populating the fields of the MBR, as presented to the operator in the overlay image data, responsive to receipt of respective user interface commands from the connected AR headset.

A17. A computer program product bearing machine-readable instructions for performing the computer-implemented process of clause A16.

B1. A computer apparatus configured to provide a process control function during manufacture of a batch of pharmaceutical product to check whether a piece of equipment has been set up correctly to carry out a manufacturing process step, the computer apparatus being configured to:
  establish a data communication connection to an augmented reality, AR, headset;
  receive scene image data from the connected AR headset of an image captured by the AR headset;
  process the received scene image data to identify an image of the piece of equipment and make a determination of its correct or incorrect set up; and
  transmit data to the connected AR headset conveying an indication of the correct or incorrect set up.

B2. The computer apparatus of clause B1, wherein the processing attempts to segment a pre-defined plurality of objects from the equipment image, wherein the processing make its determination of correct or incorrect set up by checking each segmented object, and wherein the transmitted data includes overlay image data for the AR headset to augment the scene by providing an indication of at least incorrectly set up segmented objects.

B3. The computer apparatus of clause B2, wherein the overlay image data provides an indication also of correctly set up objects.

B4. The computer apparatus of clause B2 or B3, wherein the transmitted data includes an indication of any of the pre-defined objects that the computer apparatus was unable to segment from the equipment image.

B5. The computer apparatus of clause B1, wherein the equipment set up involves arrangement of vials in set locations in relation to the equipment, and the computer apparatus is further configured to:
  process the received scene image data to identify any vials found in the scene and to identify whether they are at their set locations, wherein making the determination of correct or incorrect equipment set up takes account of whether the vials are at their set locations.

B6. The computer apparatus of clause B6, wherein the equipment set up involves arrangement of vials in relation to the equipment, and the computer apparatus is further configured to:
  process the received scene image data to perform vial identification on any vials found in the scene image data by reading a machine-readable code attached to any such vial; and in response thereto
  transmit data to the connected AR headset providing feedback information extracted through each code.

B7. The computer apparatus of clause B1, wherein the equipment set up involves removal of an item from the equipment, and the computer apparatus is further configured to segment the image to identify whether the item has been removed or is still present, and wherein the transmitted data conveys an indication of a need for item removal.

B8. The computer apparatus of clause B7, wherein the transmitted data includes overlay image data for the AR headset to augment the scene by providing an indication of an item that is still in place.

B9. The computer apparatus of clause B1, wherein the equipment set up involves correct operation of a spray nozzle, and the computer apparatus is further configured to receive scene image data from the connected AR headset of an image captured by the AR headset of a spray emission from the nozzle, and to assess whether the spray emission has a shape that falls within specification.

B10. The computer apparatus of clause B1,
  wherein the computer apparatus is further configured to generate a batch record, BR, during manufacture of the batch of pharmaceutical product by populating a master batch record, MBR, the computer apparatus further comprising:
  a process data structure defining a sequence of manufacturing process steps required to be carried out to manufacture a batch, the batch manufacturing process steps involving respective operator actions, and the manufacturing process steps including said one relating to the equipment set up;
  a mapping data structure that provides links between ones of the operator actions to ones of the content items and associated fields;
  an MBR comprising a plurality of content items and associated fields, wherein the fields are to be populated as an operator progresses through the operator actions;
  the computer apparatus being configured to:
  transmit overlay image data to the connected AR headset, the overlay image data presenting ones of the content items and associated fields to the operator in a way that follows the operator's progression through the operator actions as determined with reference to the mapping data structure and that is responsive to the operator populating the MBR fields; and
  populate fields of the MBR, as presented to the operator in the overlay image data, responsive to receipt of the user interface commands B11. A computer-implemented process for providing a process control function during manufacture of a batch of pharmaceutical product to check whether a piece of equipment has been set up correctly to carry out a manufacturing process step, the process comprising:
- establishing a data communication connection between a computer apparatus and an augmented reality, AR, headset;
- transmitting scene image data from the AR headset to the computer apparatus of an image captured by the AR headset;
- processing the received scene image data by the computer apparatus to identify an image of the piece of equipment and making a determination of its correct or incorrect set up; and
- transmitting data from the computer apparatus to the connected AR headset conveying an indication of the correct or incorrect set up.

B12. A computer program product bearing machine-readable instructions for performing the computer-implemented process of clause B11.

It will be clear to one skilled in the art that many improvements and modifications can be made to the foregoing exemplary embodiment without departing from the scope of the present disclosure.

What is claimed is:

1. A computer apparatus configured to generate a batch record, BR, during manufacture of a batch of pharmaceutical product by populating a master batch record, MBR, the BR-generating computer apparatus comprising:
- a process data structure defining a sequence of manufacturing process steps required to be carried out to manufacture a batch, the batch manufacturing process steps involving respective operator actions, wherein the operator actions include performing at least one of a chromatographic and spectroscopic analysis of the batch using a chromatographic or a spectroscopic instrument;
- an MBR comprising a plurality of content items and associated fields, wherein the fields are to be populated as an operator progresses through the operator actions, the MBR including a group of fields relating to the analysis;
- a mapping data structure that provides links between ones of the operator actions to ones of the content items and associated fields, including for the analysis; and
- a control module configured to:
- establish a data communication connection to a handheld computer apparatus of an operator responsible for manufacturing the batch;
- receive scene image data from the operator's handheld computer apparatus of a graph image captured by the operator's handheld computer apparatus showing results of the analysis;
- process the received scene image data to extract a graph and associated graph metadata from the graph image, wherein the graph includes a plurality of peaks;
- interpret the peaks of the graph with reference to the graph metadata to obtain peak data;
- populate the analysis fields with reference to the mapping data structure with the graph, metadata associated with the graph and peak data associated with the graph;
- transmit image data to the operator's handheld computer apparatus to present to the operator the populated analysis fields; and
- receive user interface commands from the operator's handheld computer apparatus to accept or reject the populated analysis fields.

2. The computer apparatus of claim 1, wherein the control module is further configured to:
- transmit image data to the operator's handheld computer apparatus to present to the operator the graph and positioned thereon a baseline which is to be taken as an ordinate zero line;
- receive user interface commands from the operator's handheld computer apparatus to reposition the baseline during which the baseline is shown interactively to the operator by amending the image data and to accept the baseline; and
- populate an analysis field with the accepted baseline.

3. The computer apparatus of claim 1, wherein the peak data includes position values for the peaks.

4. The computer apparatus of claim 1, wherein the peak data includes integral values for the peaks.

5. The computer apparatus of claim 1, wherein the control module is further configured to assign attribute labels to at least some of the peaks.

6. The computer apparatus of claim 5, wherein the attribute labels are assigned to peaks by the batch record generating computer apparatus:
- processing the graph;
- receiving user interface commands from the operator's handheld computer apparatus that specify the attribute label assignment; and/or
- processing the graph image, since the attribute label assignment was already displayed in the graph image captured by the operator's handheld computer apparatus, and can be extracted therefrom.

7. The computer apparatus of claim 6, wherein the control module is further configured to determine relative abundance values between the attributes based on a comparison of the peak integral values.

8. The computer apparatus of claim 1, wherein the control module is further configured to:
- interpret the graph with reference to pre-existing and already interpreted graphs stored in a graph library, wherein the pre-existing graphs are selected based on being from the same kind of analysis using the same kind of instrument on a different batch of the same pharmaceutical product.

9. The computer apparatus of claim 1, wherein the control module is further configured to:
- perform a quality control, QC, check of the batch based on an automated analysis of what has been entered in the analysis fields of the BR, wherein the quality control check compares the analysis field entries with what is permitted in those field entries according to a specification that forms part of the MBR; and
- output a QC check outcome selected from the following:
- the results indicate that the batch meets specification; and
- the results indicate that the batch does not meet specification; and optionally also:
- the results indicate that the batch may not meet specification; and/or
- the results indicate a systematic error in the completion of the BR.

10. The computer apparatus of a claim 9, wherein the control module is further configured to:
- transmit the BR and QC check outcome to a workstation for review by a qualified person, QP;
- receive a batch release decision from the workstation and enter it in a corresponding field of the BR.

11. The computer apparatus of claim 10, wherein the control module is further configured to:
- record at least a subset of scene image data received from the operator's handheld computer apparatus during the manufacture of the batch of pharmaceutical product, said recorded scene image data including video footage; and
- transmit at least some of the recorded scene image data to the workstation for review by the QP.

12. The computer apparatus of claim 10, wherein the control module is further configured to:
- establish a live audio communication channel between the QP workstation and the operator's handheld computer apparatus to permit the QP to speak with the operator; and
- establish a live video communication channel for transmitting live video feed from the operator's handheld computer apparatus to the QP workstation, thus enabling the QP to view a live video feed from a forward-facing camera of the operator's handheld computer apparatus while speaking with the operator.

13. The computer apparatus of claim 1, wherein the operator's handheld computer apparatus is selected from the group consisting of: a tablet computer, a mobile phone and a laptop computer.

14. A computer-implemented process for generating a batch record, BR, by populating a master batch record, MBR, stored on a computer apparatus as part of manufacture of a batch of pharmaceutical product by an operator, the operator being provided with a handheld computer apparatus, the process comprising:
- providing a process data structure defining a sequence of manufacturing process steps required to be carried out to manufacture a batch, the batch manufacturing process steps involving respective operator actions, wherein the operator actions include performing at least one of a chromatographic and spectroscopic analysis of the batch using a chromatographic or a spectroscopic instrument;
- establishing a data communication connection between the operator's handheld computer apparatus and the batch record generating computer apparatus configured to control the generation of the BR during manufacture;
- providing the batch record generating computer apparatus with an MBR comprising a plurality of content items and associated fields, wherein the fields are to be populated as an operator progresses through the operator actions, the MBR including a group of fields relating to the analysis;
- providing the batch record generating computer apparatus with a mapping data structure that provides links between ones of the operator actions to ones of the MBR content items and associated fields, including for the analysis;
- processing received scene image data to extract a graph and associated graph metadata from the graph image, wherein the graph includes a plurality of peaks;
- interpreting the peaks of the graph with reference to the graph metadata to obtain peak data;
- populating the analysis fields with reference to the mapping data structure with the graph, the graph metadata and graph peak data;
- transmitting image data to the operator's handheld computer apparatus to present to the operator the populated analysis fields; and
- receiving user interface commands from the operator's handheld computer apparatus to accept or reject the populated analysis fields.

15. The computer-implemented process of claim 14, wherein the operator's handheld computer apparatus is selected from the group consisting of: a tablet computer, a mobile phone and a laptop computer.

16. A non-transitory computer readable medium storing instructions for performing a computer-implemented process for generating a batch record, BR, by populating a master batch record, MBR, stored on a computer apparatus as part of manufacture of a batch of pharmaceutical product by an operator, the operator being provided with a handheld computer apparatus, the instructions comprising:
- one or more instructions which, when executed by one or more processors, cause the one or more processors to:
- provide a process data structure defining a sequence of manufacturing process steps required to be carried out to manufacture a batch, the batch manufacturing process steps involving respective operator actions, wherein the operator actions include performing at least one of a chromatographic and spectroscopic analysis of the batch using a chromatographic or a spectroscopic instrument;
- establish a data communication connection between the operator's handheld computer apparatus and the batch record generating computer apparatus configured to control the generation of the BR during manufacture;
- provide the batch record generating computer apparatus with an MBR comprising a plurality of content items and associated fields, wherein the fields are to be populated as an operator progresses through the operator actions, the MBR including a group of fields relating to the analysis;
- provide the batch record generating computer apparatus with a mapping data structure that provides links between ones of the operator actions to ones of the MBR content items and associated fields, including for the analysis;
- process the received scene image data to extract a graph and associated graph metadata from the graph image, wherein the graph includes a plurality of peaks;
- interpret the peaks of the graph with reference to the graph metadata to obtain peak data;
- populate the analysis fields with reference to the mapping data structure with the graph, the graph metadata and graph peak data;
- transmit image data to the operator's handheld computer apparatus to present to the operator the populated analysis fields; and
- receive user interface commands from the operator's handheld computer apparatus to accept or reject the populated analysis fields.

17. The non-transitory computer readable medium of claim 16, wherein the operator's handheld computer apparatus is selected from the group consisting of: a tablet computer, a mobile phone and a laptop computer.

* * * * *